United States Patent
Carroll et al.

(10) Patent No.: US 8,173,687 B2
(45) Date of Patent: *May 8, 2012

(54) COMPOUNDS AS CANNABINOID RECEPTOR LIGANDS

(75) Inventors: William A. Carroll, Evanston, IL (US); Michael J. Dart, Highland Park, IL (US); Jennifer M. Frost, Grayslake, IL (US); Teodozyj Kolasa, Lake Villa, IL (US); Steven P. Latshaw, Round Lake Beach, IL (US); Bo Liu, Waukegan, IL (US); Meena V. Patel, Green Oaks, IL (US); Arturo Perez-Medrano, Grayslake, IL (US); Xueqing Wang, Evanston, IL (US)

(73) Assignee: Abbott Laboratories, Abbott Park, IL (US)

( * ) Notice: Subject to any disclaimer, the term of this patent is extended or adjusted under 35 U.S.C. 154(b) by 140 days.

This patent is subject to a terminal disclaimer.

(21) Appl. No.: 12/539,120

(22) Filed: Aug. 11, 2009

(65) Prior Publication Data

US 2010/0041720 A1 Feb. 18, 2010

Related U.S. Application Data

(60) Provisional application No. 61/089,114, filed on Aug. 15, 2008.

(51) Int. Cl.
*A61K 31/433* (2006.01)
*C07D 285/12* (2006.01)

(52) U.S. Cl. ........ 514/363; 548/125; 548/136; 548/138; 514/361

(58) Field of Classification Search ............. 548/125, 548/136, 138; 514/361, 363
See application file for complete search history.

(56) References Cited

U.S. PATENT DOCUMENTS

| | | | |
|---|---|---|---|
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 7,872,033 B2* | 1/2011 | Carroll et al. | 514/372 |
| 7,875,639 B2* | 1/2011 | Florjancic et al. | 514/367 |
| 7,875,640 B2* | 1/2011 | Kolasa et al. | 514/370 |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |

FOREIGN PATENT DOCUMENTS

| | | |
|---|---|---|
| EP | 1820504 A1 | 8/2007 |
| WO | WO-9507271 A1 | 3/1995 |
| WO | WO-9710223 A1 | 3/1997 |
| WO | WO-2005099353 A2 | 10/2005 |
| WO | WO-2006008754 A1 | 1/2006 |
| WO | WO2006051704 A1 | 5/2006 |
| WO | WO-2008121558 A1 | 10/2008 |
| WO | WO-2008130953 A2 | 10/2008 |

OTHER PUBLICATIONS

Kolasa et al (2008): STN International HCAPLUS database, (Columbus, Ohio), Accession No. 2008:1184581.*
Clayton, et al., "CB1 and CB2 Cannabinoid Receptors are Implicated in Inflammatory Pain," Pain, 2002, vol. 96(3), pp. 253-260.
International Search Report for Application No. PCT/US08/057460, mailed on Aug. 20, 2008, 3 pages.
Li, et al., "An Improved Synthesis of Pyran-3,5-Dione: Application to the Synthesis of Abt-598, A Potassium Channel Opener, Via Hantzsch Reaction," Journal of Organic Chemistry, 2006, vol. 71 (4), pp. 1725-1727.
Arevalo-Martin A. et al., "Therapeutic Action of Cannabinoids in a Murine Model of Multiple Sclerosis," Journal of Neuroscience, 2003, vol. 23 (7), pp. 2511-2516.
Benito C. et al, "Cannabinoid CB2 Receptors and Fatty Acid Amide Hydrolase Are Selectiveiy Overexpressed in Neuritic Plaque-Associated Glia in Alzheimer's Disease Brains," Journal of Neuroscience, 2003, vol. 23 (35), pp. 11136-11141.
Berge S. M., et al., "Pharmacetical Salts" J Pharmaceutical Sciences, 1977, 66 (1), 1-19.
Beylot M. et el., In vivo studies of intrahepatic metaboilc pathways, Diabetes Metab., 1997, 23 (3), 251-257.
Blagojevic N. et al., "Topics in Dosimetry & Treatment Planning for Neutron Capture Therapy," 1994, vol. 23, Zamenhof R.G., Solares G.R. and Harling O.K., eds., Advanced Medical Publishing, Madison Wis, pp. 125-134.
Blake et al., "Studies with deuterated drugs," J. Pharm. Sci. 1975, vol. 64 (3), pp. 367-391.
Bouchard J. F et al., "Contribution of endocannabinoids in the endothelial protection afforded by ischemic preconditioning in the isolated rat heart," Life Sciences, 2003, vol. 72, 1859-1870.

(Continued)

*Primary Examiner* — Golam M M Shameem
(74) *Attorney, Agent, or Firm* — Nancy J. Gettel; Sonali Srivastava

(57) ABSTRACT

Disclosed herein are cannabinoid receptor ligands of formula (I)

wherein Y, $X^1$, $X^2$, $X^3$, $R^1$, and $R^2$ are as defined in the specification. Compositions comprising such compounds, and methods for treating conditions and disorders using such compounds and compositions are also disclosed.

16 Claims, No Drawings

OTHER PUBLICATIONS

Boyle W. J. et al., "Osteoclast differentiation and activation," Nature, 2003, vol. 423, pp. 337-342.

Brennan T. J. et al., "Characterization of a rat model of incisional pain," Pain, 1996, vol. 64, pp. 493-501.

Brickner S. J. et al., "Synthesis and antibacterial activity of U-100592 and U-100786, two oxazolidinone antibacterial agents for the potential treatment of multidrug-resistant gram-positive bacterial infections," J Med Chem, 1976, vol. 39 (3), pp. 673.

Buckley N. E, et al., "Immunomodulation by cannabinoids is absent in mice deficient for the cannabinoid CB receptor," European Journal of Pharmacology. 2000, vol. 396, pp. 141-149.

Carlisle S. J. et al., "Differential expression of the CB2 cannabinoid receptor by rodent macrophages and macrophage-like cells in relation to cell activation," International Immunopharmacology, 2002, vol. 2, pp. 69.

Carrier E. J. et al., "Endocannabinoids in Neuroimmunology and Stress," Current Drug Targets CNS & Neurological Disorders, 2005, vol. 4, pp. 657-665.

Casanova M. L. et al., "Inhibition of skin tumor growth and angiogenesis in vivo by activation of cannabinoid receptors," Journal of Clinical Investigation, 2003 vol. 111, pp. 43-50.

Chaplan S. R. et al., "Quantitative assessment of tactile allodynia in the rat paw," Journal of Neuroscience Methods, 1994, vol. 53, pp. 55-63.

Cichewicz D. L. et al., "Synergistic interactions between cannabinoid and opioid analgesics," Life Sciences, 2004, vol. 74, pp. 1317-1324.

Czajka D. M., "Effect of deuterium oxide on the reproductive potential of mice," Ann NY Acad Sci, 1960, vol. 84, pp. 770-779.

Czajka D. M., et al., "Physiological effects of deuterium on dogs", Am, J. Physiol, 1961, vol. 201, pp. 357-362.

Dixon W. J. et al., "Efficient analysis of experimental observations," Annual Review of Pharmacology and Toxicology, 1980, vol. 20, pp. 441-462.

Filippo C. D. et al., "Cannabinoid CB2 receptor activation reduces mouse myocardial ischemie-reperfusion injury: involvement of cytokine/chemokines and PMN" Journal of Leukocyte Biology, 2004, vol. 75, pp. 453-459.

Foster A.B., "Deuterium Isotope Effects in the Metabolism of Drugs and Xenobiotics: Implications for Drug Design" in: Advances in Drug Research, Harper, ed., 1985, vol. 14, Academic Press, pp. 2-36.

Galiêgue et al., "Expression of central and peripheral cannabinoid receptors in human immune tissues and leukocyte subpopulations," European Journal of Biochemistry, 1995, vol. 232, pp. 54-61.

Greene T. W. et al., "Protective Groups in Organic Synthesis," 1999, Ed. 3, John Wiley & Sons, pp. 494-653.

Grotenhermen F. et al., "IACM 2nd Conference on Cannabinoids in Medicine," Expert Opinion in Pharmacotherapy, 2003, vol. 4 (12), pp. 2367-2371.

Hanus L. et al., "HU-308: A specific agonist for CB 2 a peripheral cannabinoid receptor," Proceedings of the National Acedemy of Science, 1999, vol. 96, pp. 14228-14233.

Hohmann A. G., et al., "Selective Activation of Cannabinoid CB2 Receptors Suppresses Hyperalgesia Evoked by Intradermal Capsaicin," Journal of Pharmacology and Experimental Therapeutics, 2004 vol. 308, pp. 446-453.

Ibrahim M. M. et al., "Activation of CB2 cannacinoid receptors by AM1241 inhibits experimental neuropathic pain: Pain inhibition by receptors not present in the CNS," Proceedings of the National Academy of Science, 2003, vol. 100 (18), pp. 10529-10533.

Ibrahim M. M. et al., "CB2 cannabinoid receptor activation produces antinociception by stimulating peripheral release of endogenous opioids," Proceedings of the National Academy of Science, 2005, vol. 102 (8), pp. 3093-3098.

Ihenetu K. et al., "Inhibition of interleukin-8 release in the human colonic epithelial cell line HT-29 by cannabinoids," European Journal of Pharmacology, 2003, vol. 468, pp. 207-215.

IUPAC Commission on Nomenclature of Organic Chemistry: Rules for the Nomenclature of Organic Chemistry Section E: Stereochemistry, Pure Appl Chem, 1976, 45, 13-30.

Joshi S. K., et al., "Comparison of Antinociceptive Actoins of Standard Analgesics in Attenuating Capsaicin and Nerve-Injury-Induced Mechanical Hypersensitivty," Neurosci, 2006, vol. 143, pp. 587-596.

Julien B et al., "Antifibrogenic Role of the Cannabinoid Receptor CB2 in the Liver," , Gastroenterology, 2005, vol. 128, pp. 742-765.

Karsak M. et al., "Cannabinold receptor type 2 gene is associated with human osteoporosis," Human Molecular Genectics, 2005, vol. 14 (22), pp. 3389-3396.

Kato et al., "Synthesis of Deuterated Mosapride Citrate," J. Labelled Comp. Radiopharmaceut, 1995, vol. 36 (10) pp. 927-932.

Kim S. H. et al., "An experimental model for peripheral neuropathy produced by segmental spinal nerve ligation in the rat," Pain, 1992, vol. 50 (3), pp. 355-363.

Kushner et al., "Pharmacological uses and perspectives of heavy water and deuterated compounds," Can J Physiol Pharmacol, 1999, vol. 77, pp. 79-88.

Lepicier P. et al., "Endocannabinoids protect the rat isolated heart against ischaemia," British Journal of Pharmacology, 2003, vol. 139, pp. 805-815.

Lizondo J. et al., "Linezolid: Oxazolidinone antibacterial", Drugs Fut, 1996, vol. 21 (11), pp. 116.

Lotersztajn S. et al., "Hepatic Fibrosis: Molecular Mechanisms and Drug Targets," Annual Review of Pharmacology and Toxicology, 2005, vol. 45, pp. 605-628.

Malan T. P. et al., "CB2 cannabinoid receptor-mediated peripheral antinociception," Pain, 2001, vol. 93, pp. 239-245.

Mallesham B. et al., "Highly efficient Cul-catalyzed coupling of aryl bromides with oxazolidinones using Buchwald's protocol: a short route to linezolid and toloxatone," Org Lett, 2003, vol. 5 (7), pp. 963-965.

Maresz K. et al., "Modulation of the cannabinoid CB2 receptor in microglial cells in response to inflammatory stimuli," Journal of Neurochemistry, 2005, vol. 95, pp. 437-445.

Mathison R. et al., "Effects of cannabinoid receptor-2 activation on accelerated gastrointestinal transit in lipopolysaccharide-treated rats," British Journal of Pharmacology, 2004, vol. 142, pp, 1247-1254.

McKallip R. J., et al., "Targeting CB2 cannabinoid receptors as a novel therapy to treat malignant lymphoblastic disease," Blood, 2002, vol. 15 (2), pp. 627-634.

Nackley A. G. et al., "Selective activation of cannabinoid CB2 receptors suppresses spinal fos protein expression and pain behavior in a rat model of inflammation," Neuroscience, 2003, vol. 119, pp. 747-757.

Ni X. et al., "Win 55212-2, a cannabinoid receptor agonist, attenuates leukocyte/endothelial interactions in an experimental autoimmune encephalomyelitis model," Multiple Sclerosis, 2004, vol. 10, pp. 158-164.

Ohta et al., "Imine derivatives as new potent and selective CB2 cannabinoid receptor agonist with an analgesic action," Bio-organic & Medicinal Chemistry, 2007, vol. 16 (3), pp. 1111-1124.

Ohta et al., "N-Alkyidenearylcarboxamides as a new potent and selective CB2 cannabinoid receptor agonist with an analgesic action," Bio-organic & Medicinal Chemistry Letters, vol. 17 (22), pp. 6299-6304, 2007.

Patel J. J. et al., "Inhibition of guinea-pig and human sensory nerve activity and the cough reflex in guinea-pigs by cannabinoid (CB2) receptor activation," British Journal of Pharmacology, 2003, vol. 140, pp. 261-268.

PCT International search report application No. PCT/US2009/053369 mailed on Oct. 22, 2009, 2 pages.

Pertwee R. G., "Cannabinoids and multiple sclerosis,"Pharmacology & Therapeutics, 2002, vol. 95, pp. 165-174.

Prescott et al., "Lipid Vesicles as Carriers for Introducing Biologically Active Materials into Cells," Methods in Cell Biology, 1976, vol. 14, Academic Press, pp. 33-71.

Quartilho A. et al., "Inhibition of Inflammatory Hyperalgesia by Activation of Peripheral CB2 Cannabinoid Receptors," Anesthesiology, 2003, vol. 99, pp. 955-960.

Ralston S. H., "Regulation of bone mass, bone loss and osteoclast activity by cannabinoid receptors," Nature Medicine, 2005, vol. 11, pp. 774-779.

Ramirez B. G. et al., "Prevention of Alzheimer's Disease Pathology by Cannabinoids: Neuroprotection Mediated by Blockade of Microglial Activation," Journal of Neuroscience, 2005, vol. 25 (8), pp. 1904-1913.

Sanchez C. et al., "Inhibition of Glioma Growth in Vivo by Selective Activation of the CB2 Cannabinoid Receptor1," Cancer Research, 2001, vol. 61, pp. 5784-5789.

Steffens S. et al., "Low dose oral cannabinoid therapy reduces progression of atherosclerosis in mice," Nature, 2005, vol. 434, pp. 782-786.

Thomson J. F., "Physiological effects of D20 in mammals," Ann. New York Acad. Sci, 1960, vol. 84, pp. 736-744.

Valenzano K. J. et al., "Pharmacological and pharmacokintetic characterization of the cannabinoid receptor 2 agonist, GW405833, utilizing rodent models of acute and chronic pain, anxiety, ataxia and catalepsy," Neuropharmacology, 2005, vol. 48, pp. 658-672.

Warhurst A. C. et al., "Interferon gamma induces differential upregulation of alpha and beta chemokine secretion in colonic epithelial cell lines," Gut, 1998, vol. 42, pp. 208-213.

Wright K. et al., "Differential Expression of Cannabinoid Receptors in the Human Colon: Cannabinoids Promote Epithelial Wound Healing," Gastroenterology, 2005, vol. 129, pp. 437-453.

Yao B. B. et al., "In vitro pharmacological characterization of AM1241: a protean agonist at the cannabinoid CB2 receptor?," Br J Pharmacol, 2006, vol. 149 (2), pp. 145-154.

Yoshihara S. et al., "Cannabinoid Receptor Agonists Inhibit Sensory Nerve Activation in Guinea Pig Airways," American Journal of Respiratory and Critical Care Medicine, 2004, vol. 170, pp. 941-946.

Yoshihara S. et al., "Endogenous Cannabinoid Receptor Agonists Inhibit Neurogenic Inflammations in Guinea Pig Airways," Allergy and Immunology, 2005, vol. 138, pp. 80-87.

Yoshihara S. et al., "The Cannabinoid Receptor Agonist WIN 55212-2 Inhibits Neurogenic Inflammations in Airway Tissues," Journal of Pharmacological Sciences, 2005, vol. 98 (1), pp. 77-82.

* cited by examiner

COMPOUNDS AS CANNABINOID RECEPTOR LIGANDS

This application claims priority to U.S. patent application Ser. No. 61/089,114 filed Aug. 15, 2008 and is incorporated herein by reference.

TECHNICAL FIELD AND BACKGROUND

The present application relates to compounds that are cannabinoid receptor ligands, compositions comprising such compounds, and methods of treating conditions and disorders using such compounds and compositions.

(−)-$\Delta^9$-Tetrahydrocannabinol ($\Delta^9$-THC), the major psychoactive constituent of marijuana, exerts a broad range of effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in pre-clinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic). Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, fibromyalgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

SUMMARY

Disclosed herein are compounds of formula (I)

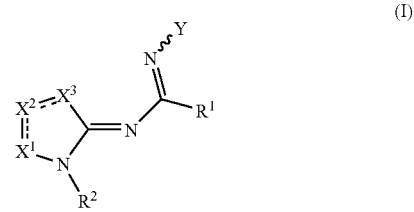

or pharmaceutically acceptable salts, solvates, prodrugs, salts of prodrugs, or any combinations thereof, wherein $R^1$ is aryl, heteroaryl or heterocycle; wherein the aryl, heteroaryl, and heterocycle are each independently unsubstituted or substituted by 1, 2, 3, 4, or 5 substituents as represented by T, wherein each T is independently selected from the group consisting of alkyl, alkenyl, alkynyl, halogen, haloalkyl, —CN, —$NO_2$, oxo, -$G^1$, -$L^1$-$A^1$, —$SR^a$, —$S(O)_2R^d$, —$S(O)_2N(R^b)(R^c)$, —$C(O)R^a$, —$C(=N-OR^{m1})R^a$, —$C(O)OR^a$, —$C(O)N(R^b)(R^c)$, —$(CR^eR^f)_r$—$OR^a$, —$(CR^eR^f)_r$—$OC(O)R^a$, —$(CR^eR^f)_r$—$OC(O)N(R^b)(R^c)$, —$(CR^eR^f)_r$—$SR^a$, —$(CR^eR^f)_r$—$S(O)_2R^d$, —$(CR^eR^f)_r$—$S(O)_2N(R^b)(R^c)$, —$(CR^eR^f)_r$—$C(O)R^a$, —$(CR^eR^f)_r$—$C(=N-OR^{m1})R^a$, —$(CR^eR^f)_r$—$C(O)OR^a$, —$(CR^eR^f)_r$—$C(O)N(R^b)(R^c)$, —$(CR^eR^f)_r$—$N(R^b)(R^c)$, —$(CR^eR^f)_r$—$N(R^c)C(O)R^a$, —$(CR^eR^f)_r$—$N(R^c)S(O)_2R^d$, —$(CR^eR^f)_r$—$N(R^c)C(O)O(R^d)$, —$(CR^eR^f)_r$—$N(R^c)C(O)N(R^b)(R^c)$, —$(CR^eR^f)_r$-$G^1$ and —$(CR^eR^f)_r$—CN;

$A^1$ is $R^a$, —$(CR^eR^f)_r$-$A^2$, —$C(O)R^a$, —$C(O)N(R^b)(R^c)$, $S(O)_2R^d$, $C(O)O(R^d)$, —$N(R^b)C(O)R^a$, —$N(R^b)C(O)OR^d$, —$N(R^b)(R^c)$, or —N=$C(R^b)(R^c)$;

$A^2$ is —$C(O)R^a$, —$S(O)_2R^d$, —$C(O)N(R^b)(R^c)$, —$C(S)N(R^b)(R^c)$, —$S(O)_2N(R^b)(R^c)$, —$C(=NOR^{m1})R^a$, —$N(R^c)C(O)R^a$, —$N(R^c)C(O)OR^d$, —$N(R^c)S(O)_2R^d$, —$N(R^c)C(O)N(R^b)(R^c)$, —$N(R^c)S(O)_2N(R^b)(R^c)$, or -$L^2$-$R^z$;

$L^1$ and $L^2$ are each independently O or $N(R^b)$;

$R^2$ is alkyl, alkenyl, alkynyl, haloalkyl, —$(CR^gR^h)_t$—$OR^k$, —$(CR^gR^h)_t$—O-$G^2$, —$(CR^gR^h)_t$—O—$(CR^gR^h)_u$-$G^2$, —$(CR^gR^h)_u$—C(O)—$R^a$, —$(CR^gR^h)_u$—C(=N—$OR^{m1}$)$R^a$, —$(CR^gR^h)_t$—$SO_2$—$R^3$, —$(CR^gR^h)_t$—$N(R^b)(R^c)$, —$(CR^gR^h)_u$-$G^3$, —$(CR^gR^h)_t$—$N(R^b)SO_2R^d$, —$(CR^gR^h)_t$—$N(R^b)COR^a$, —$(CR^gR^h)_t$—$N(R^b)CON(R^b)(R^c)$, —$(CR^gR^h)_t$—$N(R^b)SO_2N(R^b)(R^c)$, —$(CR^gR^h)_u$—$SO_2N(R^b)(R^c)$, —$(CR^gR^h)_u$—$C(O)N(R^b)(R^c)$, —$(CR^gR^h)_u$—$OC(O)N(R^b)(R^c)$, or —$(CR^gR^h)_u$—CN;

$X^1$ is N, and $X^3$ is O or S wherein the bond between $X^1$ and $X^2$ is a double bond and the bond between $X^2$ and $X^3$ is a single bond; or $X^1$ is $CR^3$, and $X^3$ is O wherein the bond between $X^1$ and $X^2$ is a double bond and the bond between $X^2$ and $X^3$ is a single bond; or $X^1$ is $NR^{3a}$ or O, and $X^3$ is $CR^5$ wherein the bond between $X^1$ and $X^2$ is a single bond and the bond between $X^2$ and $X^3$ is a double bond;

$X^2$ is $CR^4$;

$R^3$ is hydrogen, alkyl, cycloalkyl, alkoxyalkyl, cyanoalkyl, or haloalkyl;

$R^{3a}$ is alkyl, cycloalkyl, alkoxyalkyl, cyanoalkyl, or haloalkyl;

$R^4$ is hydrogen, alkyl, alkylcarbonyl, alkenyl, alkynyl, cycloalkyl, cycloalkylalkyl, alkoxyalkyl, hydroxyalkyl, haloalkyl, halo, cyano, cyanoalkyl, or monocyclic heterocycle;

$R^5$ is hydrogen, alkyl, haloalkyl, halo, cyano, or alkoxyalkyl;

Y is CN or $OR^y$ $R^y$ is alkyl, $G^5$, or —$(CR^pR^q)_v$-$G^6$;

$G^1$, $G^2$ and $G^3$, at each occurrence, are each independently aryl, heteroaryl, cycloalkyl, cycloalkenyl, or heterocycle; wherein $G^1$, $G^2$, and $G^3$ are each independently unsubstituted or substituted with 1, 2, 3, 4, or 5 substituents independently selected from the group consisting of $G^4$, alkyl, alkenyl, alkynyl, halo, haloalkyl, =N—CN, =N—$OR^{m1}$, —CN, oxo, —$NO_2$, —$OR^m$, —$OC(O)R^m$, —$OC(O)N(R^m)_2$, —$S(O)_2R^n$, —$S(O)_2N(R^m)_2$, —$C(O)R^m$, —$C(O)OR^m$, —$C(O)N(R^m)_2$, —$N(R^m)_2$, —$N(R^m)C(O)R^m$, —$N(R^m)S(O)_2R^n$, —$N(R^m)C(O)O(R^n)$, —$N(R^m)C(O)N(R^m)_2$, —$(CR^iR^j)_w$—$OR^m$, —$(CR^iR^j)_w$—$OC(O)R^m$, —$(CR^iR^j)_w$—$OC(O)N(R^m)_2$, —$(CR^iR^j)_w$—$S(O)_2R^n$, —$(CR^iR^j)_w$—$S(O)_2N(R^m)_2$, —$(CR^iR^j)_w$—$C(O)R^m$, —$(CR^iR^j)_w$—$C(O)OR^m$, —$(CR^iR^j)_w$—$C(O)N(R^m)_2$, —$(CR^iR^j)_w$—$N(R^m)_2$, —$(CR^iR^j)_w$—$N(R^m)C(O)R^m$, —$(CR^iR^j)_w$—$N(R^m)S(O)_2R^n$, —$(CR^iR^j)_w$—$N(R^m)C(O)O(R^n)$, —$(CR^iR^j)_w$—$N(R^m)C(O)N(R^m)_2$, and —$(CR^iR^j)_w$—CN;

$R^p$ and $R^q$, at each occurrence, are each independently hydrogen or alkyl;

r and u, at each occurrence, are each independently 1, 2, 3, 4, 5, or 6;

t, at each occurrence, is independently 2, 3, 4, 5, or 6;

v is 1 or 2;

each occurrence of w is independently 1, 2 or, 3;

$G^4$ is monocyclic heterocycle, monocyclic heteroaryl, or monocyclic cycloalkyl;

$G^5$ and $G^6$, are each a monocyclic ring independently selected from the group consisting of cycloalkyl, heterocycle, heteroaryl, and phenyl;

$R^a$ and $R^c$, at each occurrence, are each independently hydrogen, alkyl, haloalkyl, alkoxyalkyl, hydroxyalkyl, cyanoalkyl, haloalkoxyalkyl, $G^1$, or —$(CR^eR^f)_r$-$G^1$;

$R^b$, at each occurrence, is independently hydrogen, alkyl, haloalkyl, alkoxyalkyl, cycloalkyl, or halo alkoxyalkyl;

$R^d$, at each occurrence, is independently alkyl, haloalkyl, alkoxyalkyl, hydroxyalkyl, cyanoalkyl, haloalkoxyalkyl, $G^1$, or —$(CR^eR^f)_r$-$G^1$;

$R^e$, $R^f$, $R^g$, $R^h$, $R^i$, and $R^j$, at each occurrence, are each independently hydrogen, alkyl, halogen, or haloalkyl;

$R^k$ is hydrogen, alkyl haloalkyl, alkoxyalkyl, or haloalkoxyalkyl;

$R^z$ is alkoxyalkyl, hydroxyalkyl, cyanoalkyl, haloalkoxyalkyl, $G^1$, or —$(CR^eR^f)_r$-$G^1$;

$R^m$, at each occurrence, is independently hydrogen, alkyl, haloalkyl, —$(CR^eR^f)_q$—$OR^{m1}$, or monocyclic cycloalkyl;

$R^{m1}$, at each occurrence, is independently hydrogen, alkyl, haloalkyl, or monocyclic cycloalkyl;

$R^n$, at each occurrence, is independently alkyl, haloalkyl, cycloalkyl, or cycloalkylalkyl; and the cycloalkyl, heterocycle, heteroaryl, and phenyl, by itself of as part of a substituent, of $R^3$, $R^{3a}$, $R^4$, $G^4$, $G^5$, $G^6$, $R^b$, $R^m$, $R^{m1}$, and $R^n$, are each independently unsubstituted or substituted with 1, 2, 3, or 4 substituents selected from the group consisting of alkyl, haloalkyl, alkoxy, halo, oxo, cyano, and hydroxy.

Another aspect relates to pharmaceutical compositions comprising therapeutically effective amount of one or more compound(s) described herein or pharmaceutically acceptable salts or solvates thereof, in combination with one or more pharmaceutically acceptable carrier(s). Such compositions can be administered in accordance with a methods described herein, typically as part of a therapeutic regimen for treatment or prevention of conditions and disorders related to cannabinoid (CB) receptor subtype $CB_2$. More particularly, the methods are useful for treating conditions related to pain such as, but not limited to, neuropathic pain, nociceptive pain, inflammatory pain, cancer pain, lower back pain, post operative pain or eye pain; inflammatory disorders, immune disorders, neurological disorders, cancers of the immune system, respiratory disorders, obesity, diabetes, cardiovascular disorders, or for providing neuroprotection.

Further, provided herein is the use of present compounds or pharmaceutically acceptable salts or solvates thereof, in the manufacture of medicaments for the treatment of the disease conditions described above, alone or in combination with one or more pharmaceutically acceptable carrier, particularly for the treatment of pain such as, but not limited to, neuropathic pain, nociceptive pain, cancer pain, inflammatory pain, eye pain, or combination thereof.

The compounds, compositions comprising the compounds, and methods for treating or preventing conditions and disorders by administering the compounds are further described herein.

These and other objects of the invention are described in the following paragraphs. These objects should not be deemed to narrow the scope of the invention.

DETAILED DESCRIPTION

Compounds of formula (I) are disclosed

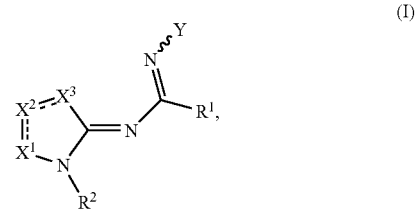

wherein Y, $X^1$, $X^2$, $X^3$, $R^1$, and $R^2$ are as defined above in the Summary of the Invention and below in the Detailed Description. Compositions comprising such compounds and methods for treating conditions and disorders using such compounds and compositions are also disclosed.

In various embodiments, the compounds may contain variables that may occur more than one time in any substituent or in the formulae herein. Definition of a variable on each occurrence is independent of its definition at another occurrence. Further, combinations of substituents and variables are permissible only if such combinations result in stable compounds. Stable compounds are compounds that can be isolated from a reaction mixture.

a. DEFINITIONS

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_4$ alkenyl" means an alkenyl group containing 2-4 carbon atoms. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double. Representative examples of alkenylene include, but are not limited to, —CH=CH— and —CH$_2$CH=CH—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 2-ethoxyethyl, 2-methoxyethyl, and methoxymethyl.

The term "alkyl" as used herein, means a straight or branched, saturated hydrocarbon chain containing from 1 to 10 carbon atoms. The term "$C_1$-$C_4$ alkyl" means a straight or branched chain hydrocarbon containing 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" means an alkyl group as defined herein, appended to the parent molecular moiety through a C(O) group. Representative examples of alkylcarbonyl include, but are not limited to, acetyl, 1-oxopropyl, 2,2-dimethyl-1-oxopropyl, 1-oxobutyl, and 1-oxopentyl.

The term "alkylene" means a divalent group derived from a straight or branched chain hydrocarbon of 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_2$-$C_4$ alkynyl" means an alkynyl group of 2 to 4 carbon atoms. Representative examples of alkynyl include, but are not limited to, acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "cyanoalkyl" as used herein, means a —CN group, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane(octahydro-2,5-methanopentalene or noradamantane), and tricyclo[3.3.1.1$^{3,7}$]decane(adamantane). The monocyclic, bicyclic, and tricyclic cycloalkyls can be unsubstituted or substituted, and are attached to the parent molecular moiety through any substitutable atom contained within the ring system.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. The term "$C_1$-$C_4$ haloalkyl" means a haloalkyl group of 1-4 carbon atoms. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "haloalkoxy" as used herein, means an alkoxy group, as defined herein, in which one, two, three, four, five or six hydrogen atoms are replaced by halogen. Representative examples of haloalkyl include, but are not limited to, 2-fluoroethoxy, 2,2,2-trifluoroethoxy, trifluoromethoxy, and difluoromethoxy.

The term "haloalkoxyalkyl" as used herein, means a haloalkoxy group, as defined herein, appended to the parent moiety through an alkyl group, as defined herein.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, 2,3-dihydrobenzofuranyl, 2,3-dihydrobenzothienyl, azabicyclo[2.2.1]heptyl (including 2-azabicyclo[2.2.1]hept-2-yl), and 2,3-dihydro-1H-indolyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-admantane(1-azatricyclo[3.3.1.1$^{3,7}$]decane), and oxa-adamantane(2-oxatricyclo[3.3.1.1$^{3,7}$]decane). The monocyclic, bicyclic, and tricyclic heterocycles can be unsubstituted or substituted, and are connected to the parent molecular moiety through any carbon atom or any nitrogen atom contained within the rings. The nitrogen and sulfur heteroatoms in the heterocycle rings may optionally be oxidized (e.g. 1,1-dioxidotetrahydrothienyl) and the nitrogen atoms may optionally be quarternized.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems. The nitrogen heteroatoms of the heteroaryl rings may optionally be oxidized, and are contemplated within the scope of the invention.

The term "heteroatom" as used herein, means a nitrogen, oxygen, or sulfur atom.

The term "hydroxyl" or "hydroxy" means a —OH group.

The term "hydroxyalkyl" means an hydroxy group, as defined herein, appended to the parent molecular moiety through an alkyl group, as defined herein. Representative examples of hydroxyalkyl include, but are not limited to, hydroxymethyl, 2-hydroxyethyl, and 3-hydroxypropyl.

The term "oxo" as used herein, means a =O group.

The terms "treat", "treating", and "treatment" refer to a method of alleviating or abrogating a disease or condition and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

b. COMPOUNDS

Certain exemplary compounds described herein have formula (I) as described above.

Particular values of variable groups in compounds of formula (I) are as follows. Such values may be used where appropriate with any of the other values, definitions, claims or embodiments defined hereinbefore or hereinafter.

$X^1$, $X^2$, and $X^3$ have values as described generally for compounds of formula (I).

Certain embodiments are directed to compounds of formula (I) wherein $X^1$ is N, and $X^3$ is O or S, the bond between $X^1$ and $X^2$ is a double bond and the bond between $X^2$ and $X^3$ is a single bond, and $X^2$ is $CR^4$. Examples of compounds thus include those of formula (II)

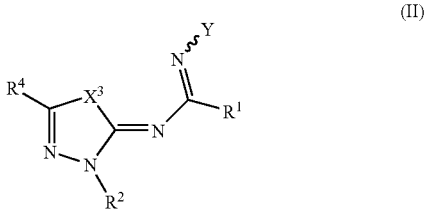

(II)

wherein $X^3$ is O or S, and $R^1$, $R^2$, Y, and $R^4$ are as disclosed in the Summary and in the embodiments described herein. In certain embodiments, $X^3$ is S.

Other embodiments are directed to compounds of formula (I) wherein $X^1$ is $CR^3$, $X^3$ is O, the bond between $X^1$ and $X^2$ is a double bond and the bond between $X^2$ and $X^3$ is a single bond, and $X^2$ is $CR^4$. Thus, examples include those of formula (III)

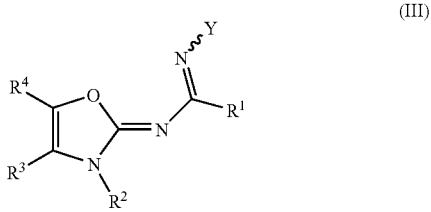

(III)

wherein $R^1$, $R^2$, Y, $R^3$, and $R^4$ are as disclosed in the Summary and in the embodiments described herein.

Yet other embodiments are directed to compounds of formula (I) wherein $X^1$ is $NR^{3a}$ or O, $X^3$ is $CR^5$, $X^2$ is $CR^4$, and the bond between $X^1$ and $X^2$ is a single bond and the bond between $X^2$ and $X^3$ is a double bond. Accordingly, examples include those of formula (IV)

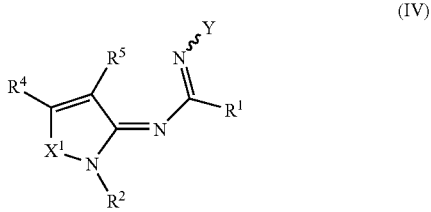

(IV)

wherein $X^1$ is $NR^{3a}$ or O, and $R^{3a}$, $R^1$, $R^2$, Y, $R^4$, and $R^5$ are as disclosed in the Summary and in the embodiments described herein. In certain embodiments, $X^1$ is $NR^{3a}$ and $R^{3a}$ is alkyl. In yet other embodiments, $X^1$ is $NR^{3a}$ and $R^{3a}$ is alkyl. Other examples include those wherein $X^1$ is O.

Within compounds of formula (I), (II), (III), and (IV), Y, $R^3$, $R^{3a}$, $R^4$, and $R^5$ have values as described in the Summary.

For example, in certain embodiments, $R^3$ is hydrogen, alkyl (e.g. $C_1$-$C_4$ alkyl such as, but not limited to, methyl, ethyl, isopropyl), monocyclic cycloalkyl (e.g. cyclopropyl, cyclobutyl, and the like), or haloalkyl (e.g. trifluoromethyl). In yet other embodiments, $R^3$ is hydrogen, alkyl (e.g. $C_1$-$C_4$ alkyl such as, but not limited to, methyl, ethyl, isopropyl), or haloalkyl e.g. trifluoromethyl).

In certain embodiments, $R^{3a}$ is alkyl or haloalkyl. For example, $R^{3a}$ is alkyl (e.g. $C_1$-$C_4$ alkyl such as, but not limited to, methyl).

Examples of $R^4$ for compounds of formula (I)-(IV) include, but are not limited to, hydrogen, alkyl, alkenyl, alkynyl, monocyclic cycloalkyl, haloalkyl, or monocyclic heterocycle. In certain embodiments, $R^4$ is hydrogen, alkyl, monocyclic cycloalkyl (e.g. cyclopropyl), or haloalkyl. For example, $R^4$ is alkyl (e.g. $C_1$-$C_4$ alkyl such as, but not limited to, methyl, ethyl, isopropyl, tert-butyl).

Examples of $R^5$ for compounds of formula (I)-(IV) include, but are not limited to, hydrogen, alkyl, haloalkyl, or halo. In certain embodiments, $R^5$ is hydrogen.

In compounds of formula (I)-(IV), Y has values as described in the Summary. For example, Y is CN. In certain embodiments, Y is $OR^y$ wherein $R^y$ is as described in the Summary. For example, $R^y$ is alkyl (e.g. $C_1$-$C_4$ alkyl such as, but not limited to, methyl).

As described generally above, $R^1$ in formula (I)-(IV) has values as described in the Summary. In certain embodiments, $R^1$ is aryl such as but not limited to phenyl, substituted by 1, 2, or 3, substituents as represented by T, and T is as described in the Summary and embodiments herein. Examples of T include, but are not limited to, halogen (e.g. F, Cl), haloalkyl (e.g. trifluoromethyl), —CN, and -$L^1$-$A^1$ wherein $L^1$ and $A^1$ are as described in the Summary and embodiments herein. For example, $L^1$ is O. In yet other embodiments, $L^1$ is $N(R^b)$ wherein $R^b$ is hydrogen or alkyl (e.g. methyl). In certain embodiments, $A^1$ is alkyl (e.g. $C_1$-$C_4$ alkyl such as, but not limited to, methyl, ethyl, isopropyl) or haloalkyl (e.g. 2-fluoroethyl). In certain embodiments, the $L^1$-$A^1$ group is located on the ortho position relative to the point of attachment to the parent moiety.

$R^2$ in compounds of formula (I)-(IV) has values as described in the Summary. For example, $R^2$ is alkyl, alkenyl, alkynyl, haloalkyl, —$(CR^gR^h)_t$—$OR^k$, —$(CR^gR^h)_t$—O-$G^2$, —$(CR^gR^h)_t$—O—$(CR^gR^h)_u$-$G^2$, —$(CR^gR^h)_u$—C(O)—$R^a$, —$(CR^gR^h)_u$—C(=N—$OR^{m1}$)$R^a$, —$(CR^gR^h)_u$-$G^3$, —$(CR^gR^h)_t$—$N(R^b)SO_2R^d$, —$(CR^gR^h)_t$—$N(R^b)COR^a$, —$(CR^gR^h)_t$—$N(R^b)CON(R^b)(R^c)$, —$(CR^gR^h)_t$—$N(R^b)SO_2N(R^b)(R^c)$, —$(CR^gR^h)_u$—$SO_2N(R^b)(R^c)$, —$(CR^gR^h)_u$—$C(O)N(R^b)(R^c)$, —$(CR^gR^h)_u$—$OC(O)N(R^b)(R^c)$, or —$(CR^gR^h)_u$—CN; $R^g$ and $R^h$ are each independently hydrogen or $C_1$-$C_4$ alkyl; $G^2$ and $G^3$, at each occurrence, are each independently monocyclic heteroaryl, monocyclic cycloalkyl, or monocyclic heterocycle; and t, u, $R^a$, $R^b$, $R^c$, $R^{m1}$, $R^k$, and $R^d$ are as described in the Summary. In certain embodiments, $R^2$ is alkyl, —$(CR^gR^h)_u$-$G^3$, or —$(CR^gR^h)_u$—CN wherein $R^g$, $R^h$, u, and $G^3$ are as described in the Summary. For example, $R^g$ and $R^h$ are each independently hydrogen or $C_1$-$C_4$ alkyl; $G^3$ is monocyclic heteroaryl, monocyclic cycloalkyl, or monocyclic heterocycle, each of which is optionally substituted as described in the Summary and embodiments herein. Examples of compounds of formula (I)-(IV) include those wherein $R^2$ is alkyl (e.g. n-butyl, isobutyl, pentyl), —$(CH_2)$-$G^3$, or —$(CH_2)_3$—CN, wherein $G^3$ is as disclosed in the Summary and embodiments herein. For example $G^3$ is an optionally substituted monocyclic heterocycle (e.g. tetrahydrofuranyl including but not limited to, tetrahydrofuran-2-yl) or an optionally substituted monocyclic heteroaryl (e.g. 1,3-thiazolyl including but not limited to, 1,3-thiazol-4-yl).

It is appreciated that the present invention contemplates compounds of formula (I)-(IV) with combinations of the above embodiments, including particular, more particular and preferred embodiments.

Accordingly, one aspect is directed to a group of compounds of formula (I) wherein $R^3$ is hydrogen, alkyl, cycloalkyl, or haloalkyl; $R^{3a}$ is alkyl or haloalkyl; $R^4$ is hydrogen, alkyl, alkenyl, alkynyl, monocyclic cycloalkyl, haloalkyl, or monocyclic heterocycle; $R^5$ is hydrogen, alkyl, haloalkyl, or halo; and $R^1$, $R^2$, and Y are as described in the Summary and in the embodiments disclosed herein.

Another aspect is directed to a group of compounds of formula (II) wherein $R^2$ is alkyl, alkenyl, alkynyl, haloalkyl, —$(CR^gR^h)_t$—$OR^k$, —$(CR^gR^h)_t$—O-$G^2$, —$(CR^gR^h)_t$—O—$(CR^gR^h)_u$-$G^2$, —$(CR^gR^h)_u$—$C(O)$—$R^a$, —$(CR^gR^h)_u$—$C(=N-OR^{m1})R^a$, —$(CR^gR^h)_u$-$G^3$, —$(CR^gR^h)_t$—$N(R^b)SO_2R^d$, —$(CR^gR^h)_t$—$N(R^b)COR^a$, —$(CR^gR^h)_t$—$N(R^b)CON(R^b)(R^c)$, —$(CR^gR^h)_t$—$N(R^b)SO_2N(R^b)(R^c)$, —$(CR^gR^h)_u$—$SO_2N(R^b)(R^c)$, —$(CR^gR^h)_u$—$C(O)N(R^b)(R^c)$, —$(CR^gR^h)_u$—$OC(O)N(R^b)(R^c)$, or —$(CR^gR^h)_u$—CN; $R^g$ and $R^h$ are each independently hydrogen or $C_1$-$C_4$ alkyl; $G^2$ and $G^3$, at each occurrence, are each independently monocyclic heteroaryl, monocyclic cycloalkyl, or monocyclic heterocycle; $R^4$ is hydrogen, alkyl, alkenyl, alkynyl, monocyclic cycloalkyl, haloalkyl, or monocyclic heterocycle; $R^1$ is phenyl substituted by 1, 2, or 3, substituents as represented by T; $X^3$ is O or S; and T, $R^k$, u, t, $R^{m1}$, $R^a$, $R^b$, $R^c$, $R^d$, and Y are as described in the Summary and in the embodiments described herein. In certain embodiments, $X^3$ is S. In certain embodiments, $R^2$, for example, is alkyl, —$(CR^gR^h)_u$-$G^3$, or —$(CR^gR^h)_u$—CN; and $R^4$ is alkyl, cycloalkyl, or haloalkyl.

Yet another aspect of the invention is directed to a group of compounds of formula (III) wherein $R^2$ is alkyl, alkenyl, alkynyl, haloalkyl, —$(CR^gR^h)_t$—$OR^k$, —$(CR^gR^h)_t$—O-$G^2$, —$(CR^gR^h)_t$—O—$(CR^gR^h)_u$-$G^2$, —$(CR^gR^h)_u$—$C(O)$—$R^a$, —$(CR^gR^h)_u$—$C(=N-OR^{m1})R^a$, —$(CR^gR^h)_u$-$G^3$, —$(CR^gR^h)_t$—$N(R^b)SO_2R^d$, —$(CR^gR^h)_t$—$N(R^b)COR^a$, —$(CR^gR^h)_t$—$N(R^b)CON(R^b)(R^c)$, —$(CR^gR^h)_t$—$N(R^b)SO_2N(R^b)(R^c)$, —$(CR^gR^h)_u$—$SO_2N(R^b)(R^c)$, —$(CR^gR^h)_u$—$C(O)N(R^b)(R^c)$, —$(CR^gR^h)_u$—$OC(O)N(R^b)(R^c)$, or —$(CR^gR^h)_u$—CN; $R^g$ and $R^h$ are each independently hydrogen or $C_1$-$C_4$ alkyl; $G^2$ and $G^3$, at each occurrence, are each independently monocyclic heteroaryl, monocyclic cycloalkyl, or monocyclic heterocycle; $R^3$ is hydrogen, alkyl, monocyclic cycloalkyl, or halo alkyl; $R^4$ is alkyl, alkenyl, alkynyl, monocyclic cycloalkyl, halo alkyl, or monocyclic heterocycle; $R^1$ is phenyl substituted by 1, 2, or 3, substituents as represented by T; and T, $R^k$, u, t, $R^{m1}$, $R^1$, $R^b$, $R^c$, $R^d$, and Y are as described in the Summary and in the embodiments described herein. In certain embodiments, $R^2$, for example, is alkyl, —$(CR^gR^h)_u$-$G^3$, or —$(CR^gR^h)_u$—CN; $R^3$, for example, is hydrogen, alkyl, or haloalkyl; and $R^4$ is alkyl, monocyclic cycloalkyl, or haloalkyl.

A further aspect is directed to a group of compounds of formula (IV) wherein $R^2$ is alkyl, alkenyl, alkynyl, haloalkyl, —$(CR^gR^h)_t$—$OR^k$, —$(CR^gR^h)_t$—O-$G^2$, —$(CR^gR^h)_t$—O—$(CR^gR^h)_u$-$G^2$, —$(CR^gR^h)_u$—$C(O)$—$R^a$, —$(CR^gR^h)_u$—$C(=N-OR^{m1})R^a$, —$(CR^gR^h)_u$-$G^3$, —$(CR^gR^h)_t$—$N(R^b)SO_2R^d$, —$(CR^gR^h)_t$—$N(R^b)COR^a$, —$(CR^gR^h)_t$—$N(R^b)CON(R^b)(R^c)$, —$(CR^gR^h)_t$—$N(R^b)SO_2N(R^b)(R^c)$, —$(CR^gR^h)_u$—$SO_2N(R^b)(R^c)$, —$(CR^gR^h)_u$—$C(O)N(R^b)(R^c)$, —$(CR^gR^h)_u$—$OC(O)N(R^b)(R^c)$, or —$(CR^gR^h)_u$—CN; $R^g$ and $R^h$ are each independently hydrogen or $C_1$-$C_4$ alkyl; $G^2$ and $G^3$, at each occurrence, are each independently monocyclic heteroaryl, monocyclic cycloalkyl, or monocyclic heterocycle; $X^1$ is O or $NR^{3a}$, $R^{3a}$ is alkyl, or haloalkyl; $R^4$ is hydrogen, alkyl, alkenyl, alkynyl, monocyclic cycloalkyl, haloalkyl, or monocyclic heterocycle; $R^5$ is hydrogen, alkyl, haloalkyl, or halo; $R^1$ is phenyl substituted by 1, 2, or 3, substituents as represented by T; and T, $R^k$, u, t, $R^a$, $R^b$, $R^c$, $R^d$, and Y are as described in the Summary and in the embodiments described herein. In certain embodiments, $R^2$, for example, is alkyl, —$(CR^gR^h)_u$-$G^3$, or —$(CR^gR^h)_u$—CN; $R^{3a}$, for example, is alkyl; $R^4$, for example, is alkyl, monocyclic cycloalkyl, or haloalkyl, and $R^5$, for example, is hydrogen.

Within each group of the compounds of formula (I)-(IV) as described in the preceding paragraphs, Y is as described in the Summary and in the embodiments described herein. Thus, examples of a subgroup of compounds of formula (I)-(IV) include those wherein Y is CN.

Examples of another subgroup of compounds of formula (I)-(IV) include those wherein Y is $OR^y$ wherein $R^y$ is as described in the Summary.

Further examples of a subgroup of compounds of formula (I)-(IV) include those wherein Y is $OR^y$ wherein $R^y$ is alkyl.

Specific embodiments of compounds contemplated as part of the invention include, but are not limited to:

N-[(3E)-2-butyl-5-tert-butylisoxazol-3(2H)-ylidene]-5-chloro-N'-cyano-2-methoxybenzenecarboximidamide;

N-[(3E)-5-tert-butyl-2-isobutylisoxazol-3(2H)-ylidene]-5-chloro-N'-cyano-2-methoxybenzenecarboximidamide;

N-[(3E)-5-tert-butyl-2-isobutylisoxazol-3(2H)-ylidene]-N'-cyano-2-ethoxy-5-(trifluoromethyl)benzenecarboximidamide;

N-[(2Z)-3-butyl-5-tert-butyl-1,3,4-thiadiazol-2(3H)-ylidene]-5-chloro-N'-cyano-2-methoxybenzenecarboximidamide;

N-[(2Z)-5-tert-butyl-3-isobutyl-1,3,4-thiadiazol-2(3H)-ylidene]-5-chloro-N'-cyano-2-methoxybenzenecarboximidamide;

N-{(3E)-5-tert-butyl-1-methyl-2-[(2R)-tetrahydrofuran-2-ylmethyl]-1,2-dihydro-3H-pyrazol-3-ylidene}-N'-cyano-2-fluoro-3-(trifluoromethyl)benzenecarboximidamide;

N-[(2Z)-5-tert-butyl-3-(1,3-thiazol-4-ylmethyl)-1,3,4-thiadiazol-2(3H)-ylidene]-5-chloro-N'-cyano-2-methoxybenzenecarboximidamide;

N-[(2Z)-5-tert-butyl-3-(3-cyanopropyl)-1,3,4-thiadiazol-2(3H)-ylidene]-5-chloro-N'-cyano-2-methoxybenzenecarboximidamide;

N-[(2)-3-butyl-5-tert-butyl-1,3,4-thiadiazol-2(3H)-ylidene]-5-chloro-N',2-dimethoxybenzenecarboximidamide; and N-{(3E)-5-tert-butyl-1-methyl-2-[(2R)-tetrahydrofuran-2-ylmethyl]-1,2-dihydro-3H-pyrazol-3-ylidene}-N'-cyano-2-(2-fluoroethoxy)-5-(trifluoromethyl)benzenecarboximidamide;

or pharmaceutically acceptable salts or solvates thereof.

Compounds of the present application may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration. It is appreciated that the ∼∼∼bond between the nitrogen atom and the functional group, Y, means that Y may orientate towards or away from the $R^1$ in formula (I)-(IV), relative to the C=N bond bearing $R^1$ and Y groups. Thus, for example, compounds of formula (I) include structures wherein Y and $R^1$ lie on the same (e.g. formula (IA)) or the opposite (e.g. formula (IB)) side of the C=N bond bearing the Y and $R^1$ groups.

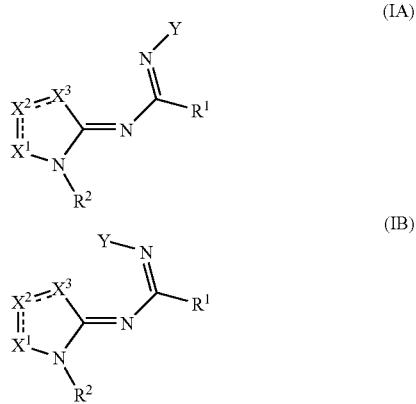

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2H$, $^3H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of CB2 ligands in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10):927-932 (1995); Kushner et al., Can. J. Physiol. Pharmacol., 77, 79-88 (1999).

In addition, non-radio active isotope containing drugs, such as deuterated drugs called "heavy drugs," can be used for the treatment of diseases and conditions related to CB2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug may alter its physicochemical properties such as pKa and lipid solubility. These effects and alterations may affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmcokinetic profile or efficacy relative to the non-istopic compound.

c. BIOLOGICAL DATA (i) In Vitro Methods—$CB_2$ Radioligand Binding Assays:

HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 µg/well for human $CB_2$) into wells of a deep well plate containing [$^3$H]CP 55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 µL/well of cold assay buffer followed by rapid vacuum filtration through a UniFilter-96 GF/C filter plates (pre-soaked in 1 mg/mL BSA for 2 hours). The bound activity was counted in a Top-Count using Microscint-20. Saturation experiments were conducted with twelve concentrations of [$^3$H]CP 55,940 ranging from 0.01 to 8 nM. Competition experiments were conducted with 0.5 nM [$^3$H]CP 55,940 and five concentrations (0.01 nM to 10 µM) of displacing ligands. The addition of 10 µM unlabeled CP 55,940 (Tocris, Ellisville, Mo.) was used to assess nonspecific binding.

HEK293 cells stably expressing rat $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 20 µg/well for rat $CB_2$) into wells of a deep well plate containing [$^3$H]CP 55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 45 min incubation at 30° C., binding reaction was terminated by the addition of 300 µl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP 55,940 ranging from 0.01 to 8 nM. Competition experiments were conducted with 0.5 nM [$^3$H] CP 55,940 and five concentrations of displacing ligands selected from the range of 0.01 nM to 10 µM. The addition of 10 µM unlabeled CP 55,940 (Tocris, Ellisville, Mo.) was used to assess nonspecific binding.

Compounds tested with the above assay have equilibrium dissociation constants ($K_i$) of less than about 1,000 nM, for example, less than about 400 nM, or less than about 200 nM, or less than about 100 nM.

(ii) Cyclase Functional Assays

The rat and human $CB_2$ and $CB_1$ cyclase functional assays were performed as described by Yao B B, Mukherjee S, Fan Y, Garrison T R, Daza A V, Grayson G K, Hooker B A, Dart M J, Sullivan J P and Meyer M D (2006) Br J Pharmacol 149: 145-154 using the HitHunter® assay kit from DiscoveRx (Fremont, Calif., USA). Briefly, cell suspensions were incubated at 37° C. for 20 minutes with variable concentrations of test ligands or 10 µM CP 55,940 positive control in the presence of a fixed concentration of forskolin (18 µM for rat $CB_2$; and 37 µM for human $CB_1$ and $CB_2$, and rat $CB_1$) in D-PBS buffer (Invitrogen, Carlsbad, Calif., USA) supplemented with BSA (0.01% final concentration). The reactions were terminated by the addition of lysis buffer and the luminescence was detected following the procedure according to the vendor's instruction. Receptor activation by ligands was expressed as percent response compared to that of 10 µM CP 55,940. $EC_{50}$ values and 95% confidence intervals were calculated using sigmoidal dose response curve fitting using Prism (GraphPad) software.

Compounds tested with the above cyclase assays are 10 to >1,000-fold more potent at rat or human $CB_2$ vs. $CB_1$ receptors.

(iii) In Vivo Data Animals

Adult male Sprague-Dawley rats (250-300 g body weight, Charles River Laboratories, Portage, Mich.) are used. Animal handling and experimental protocols are approved by the Institutional Animal Care and Use Committee (IACUC) at Abbott Laboratories. For all surgical procedures, animals are maintained under isoflurane anesthesia (4-5% to induce, 1-3% to maintain), and the incision sites are sterilized using a 10% povidone-iodine solution prior to and after surgeries.

Incision Model of Postoperative Pain

A skin incision model of postoperative pain can be produced using the procedures as described in Brennan et al., 1996, Pain, 64, 493. All rats are anesthetized with isofluorane delivered via a nose cone. Right hind paw incision is performed following sterilization procedures. The plantar aspect of the left hind paw is placed through a hole in a sterile plastic drape. A 1-cm longitudinal incision is made through the skin and fascia of the plantar aspect of the hind paw, starting 0.5 cm from the proximal edge of the heel and extending towards the toes, the plantar muscle is elevated and incised longitudinally leaving the muscle origin and insertion points intact. The skin is then closed with two mattress sutures (5-0 nylon). After surgery, animals are then allowed to recover for 2 hours, at which time tactile allodynia is assessed as described below. To evaluate the anti-nociceptive effects, animals are i.p. administered vehicle or test compound 90 minutes following skin incision and tactile allodynia can be assessed 30 minutes after compound administration.

Tactile allodynia can be measured using calibrated von Frey filaments (Stoelting, Wood Dale, Ill.) as described in Chaplan, S. R., F. W. Bach, J. M. Pogrel, J. M. Chung and T. L. Yaksh, 1994, Quantitative assessment of tactile allodynia in the rat paw, J. Neurosci. Methods, 53,55. Rats are placed into inverted individual plastic cage (20×12.5×20 cm) on top of a suspended wire mesh grid, and acclimated to the test chambers for 20 minutes. The von Frey filaments are applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses include an abrupt withdrawal of the hind paw from the stimulus, or flinching behavior immediately following removal of the stimulus. A 50% withdrawal threshold is determined using an up-down procedure (Dixon, W. J., 1980, Efficient analysis of experimental observations, Ann. Rev. Pharmacol. Toxicol. 20, 441).

Spinal Nerve Ligation Model of Neuropathic Pain

A model of spinal nerve ligation-induced (SNL model) neuropathic pain as originally described by Kim and Chung (Kim, S. H. and J. M. Chung, 1992, Pain 50, 355) can be used to test the compounds of the present application The left L5 and L6 spinal nerves of the rat are isolated adjacent to the vertebral column and tightly ligated with a 5-0 silk suture distal to the DRG, and care is taken to avoid injury of the L4 spinal nerve. Sham rats undergo the same procedure, but without nerve ligation. All animals are allowed to recover for at least one week and not more than three weeks prior to assessment of tactile allodynia.

Tactile allodynia can be measured using calibrated von Frey filaments (Stoelting, Wood Dale, Ill.) as described in Chaplan, S. R., F. W. Bach, J. M. Pogrel, J. M. Chung and T. L. Yaksh, 1994, Quantitative assessment of tactile allodynia in the rat paw, J. Neurosci. Methods, 53,55. Rats are placed into inverted individual plastic containers (20×12.5×20 cm) on top of a suspended wire mesh grid, and acclimated to the test chambers for 20 minutes. The von Frey filaments are presented perpendicularly to the plantar surface of the selected hind paw, and then held in this position for approximately 8 sec with enough force to cause a slight bend in the filament. Positive responses include an abrupt withdrawal of the hind paw from the stimulus, or flinching behavior immediately following removal of the stimulus. A 50% withdrawal threshold can be determined using an up-down procedure (Dixon, W. J., 1980, Efficient analysis of experimental observations, Ann. Rev. Pharmacol. Toxicol., 20, 441. Only rats with a baseline threshold score of less that 4.25 g are used in the study, and animals demonstrating motor deficit are excluded. Tactile allodynia thresholds are also assessed in several control groups, including naive, sham-operated, and saline infused animals as well as in the contralateral paws of nerve-injured rats.

Capsaicin-Induced Secondary Mechanical Hypersensitivity:

Rats were allowed to acclimate to the study room for 1 hour. They were then briefly restrained, and capsaicin was administered at 10 µg in 10 µL of vehicle (10% ethanol and 2-hydroxypropyl cyclodextrin) by intraplantar injection into the center of the right hind paw. Secondary mechanical hyperalgesia was measured at the heel away from the site of injection at 180 min following capsaicin (Joshi et al 2006, Neuroscience 143, 587-596). Compounds were injected (i.p.) 30 min before testing (150 min post-capsaicin).

Tactile allodynia was measured as described above. Compounds tested showed a statistically significant change in paw withdrawal latency versus a saline vehicle at less than about 300 micromoles/kg, for example, at less than about 100 micromoles/kg.

d. METHODS OF USING THE COMPOUNDS

One embodiment provides methods for treating pain (for example, inflammatory pain, neuropathic pain, nociceptive pain, cancer pain, lower back pain, post-operative pain, eye pain) in a mammal (including human) in need of such treatment. The methods comprise administering to the mammal therapeutically effective amount(s) of one or more compounds as described herein, or pharmaceutically acceptable salts or solvates thereof, alone or in combination with one or more pharmaceutically acceptable carrier(s). The method further comprises administration of compounds of the invention as a single dose. The method also comprises repeated or chronic administration of compounds of the invention over a period of days, weeks, months, or longer. In certain embodiments, the method comprises administering to the mammal a therapeutically effective amount of any of the compounds as described herein, or a pharmaceutically acceptable salt thereof, in combination with one or more nonsteroidal anti-inflammatory drug (NSAID), or other analgesics (for example, acetaminophen or opioids), or combinations thereof.

Another embodiment of the present invention provides methods for treating disorders selected from the group consisting of inflammatory disorders, immune disorders, neurological disorders, cancers of the immune system, respiratory disorders, and cardiovascular disorders in a mammal in need of such treatment. The method comprises administering to the mammal therapeutically effective amount of one or more compound described herein or pharmaceutically acceptable salts or solvates thereof, alone or in combination with one or more pharmaceutically acceptable carrier(s).

Yet another embodiment relates to methods for providing neuroprotection in a mammal in need of such treatment. These methods comprise administering to the mammal therapeutically effective amounts of one or more compounds described herein or pharmaceutically acceptable salts or solvates thereof, alone or in combination with one or more pharmaceutically acceptable carrier(s).

Another embodiment provides method for increasing the therapeutic effectiveness or potency of compounds of the invention by repeated or chronic administration over a period of days, weeks, or months.

In addition to the data contained herein, several lines of evidence support the assertion that $CB_2$ receptors play a role in analgesia. HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabiniod ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260).

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators may be useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system.-Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands may be clinically useful for the treatment of neuroinflammation.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators may provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators may possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators may represent a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu. Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators may represent a unique approach for the treatment of liver fibrosis.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators may have utility as antitussive agents for the treatment of pulmonary inflammation, chronic cough, and a variety of airway inflammatory diseases including but not limited to asthma, chronic obstructive pulmonary disease, and pulmonary fibrosis.

There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators may be useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor may be clinically useful for the treatment of atheroscelorsis.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators may have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators may have utility for the treatment or prophylaxis of cardiovascular disease and the development of myocardial infarction.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of compounds of the invention may be required to achieve the desired therapeutic response. "Repeated or chronic administration" refers to the administration of compounds of the invention daily (i.e., every day) or intermittently (i.e., not every day) over a period of days, weeks, months, or longer. In particular, the treatment of chronic painful conditions is anticipated to require such repeated or chronic administration of compounds of the invention. Compounds of the invention may become more effective upon repeated or chronic administration such that the therapeutically effective doses on repeated or chronic administration may be lower than the therapeutically effective dose from a single administration.

Compounds of the invention can also be administered as a pharmaceutical composition comprising the compounds of interest in combination with one or more pharmaceutically acceptable carriers. The phrase "therapeutically effective amount" of the refers to that amount of the compound being administered sufficient to prevent development of or alleviate to some extent one or more of the symptoms of the condition or disorder being treated at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

Compounds of the invention may be administered alone, or in combination with one or more other compounds of the invention, or in combination (i.e. co-administered) with one or more additional pharmaceutical agents. For example, one or more compounds, or pharmaceutically acceptable salts or solvates thereof, may be administered in combination with one or more analgesic (e.g. acetaminophen, opioid such as morphine), or with one or more nonsteroidal anti-inflammatory drug (NSAID), or combinations thereof. Non limiting examples of NSAID include, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds of invention and one or more additional pharmaceutical agents, as well as administration of the compounds of the invention and each additional pharmaceutical agent, in its own separate pharmaceutical dosage formulation. For example, a compound of the invention and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, compounds of the invention and one or more additional pharmaceutical agents may be administered at essentially the same time (e.g., concurrently) or at separately staggered times (e.g., sequentially).

The total daily dose of the compounds of this invention administered to a human or other animal range from about 0.01 mg/kg body weight to about 100 mg/kg body weight. More preferable doses can be in the range of from about 0.03 mg/kg body weight to about 30 mg/kg body weight. If desired, the effective daily dose can be divided into multiple doses for purposes of administration. Consequently, single dose compositions may contain such amounts or submultiples thereof to make up the daily dose. It is understood that the effective daily dose may vary with the duration of the treatment.

e. PHARMACEUTICAL COMPOSITIONS

The present invention further provides pharmaceutical compositions that comprise compounds of the present invention or a pharmaceutically acceptable salt or solvate thereof. The pharmaceutical compositions comprise compounds of the present invention that may be formulated together with one or more non-toxic pharmaceutically acceptable carriers.

Another aspect provides pharmaceutical compositions comprising one or more compounds described herein, or pharmaceutically acceptable salts or solvates thereof, and one or more pharmaceutically acceptable carriers, alone or in combination with one or more analgesics (e.g. acetaminophen), or in combination with one or more nonsteroidal anti-inflammatory drug (NSAID), or a combination thereof.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

The present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

Contemplated herein are compounds of the invention formed by synthetic means or formed by in vivo biotransformation of a prodrug.

The compounds can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. GENERAL SYNTHESIS

Compounds described herein when prepared by synthetic processes or by metabolic processes are encompassed within the scope of this application. Preparation of the compounds by metabolic processes includes those occurring in the human or animal body (in vivo) or processes occurring in vitro.

The compounds may be prepared by a variety of processes well known for the preparation of compounds of this class. For example, compounds disclosed herein wherein the groups Y, $X^1$, $X^2$, $X^3$, $R^1$, $R^2$, $R^3$, $R^{3a}$, $R^4$, $R^5$, T, $L^1$, and $A^1$, have the meanings as set forth in the summary section unless otherwise noted, can be synthesized as shown in Schemes 1-9.

Abbreviations which have been used in the descriptions of the Schemes and the Examples that follow are: DMF for N,N-dimethylformamide, DMSO for dimethyl sulfoxide, EtOAc for ethyl acetate, Et$_3$N for triethylamine, MeOH for methanol, THF for tetrahydrofuran, Ms for methylsulfonyl, Ts for 4-toluenesulfonyl, Et for ethyl, Et$_2$O for diethyl ether, and Pd$_2$(dba)$_3$ for tris(dibenzylideneacetone)dipalladium(0).

Scheme 1

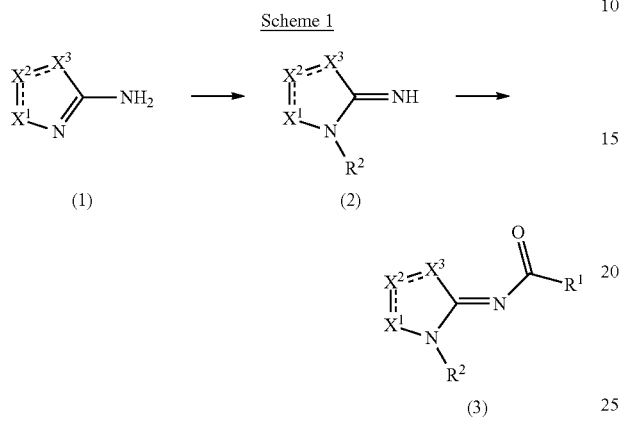

Compounds of formula (3) may be prepared according to the 2-step method illustrated in Scheme 1. Amino compounds of formula (1) can be first reacted with compounds of formula $R^2$—$X^{101}$, wherein $X^{101}$ is Cl, Br, I, OTs, or OMs, to form the intermediate (2). This reaction may be performed either neat or in a solvent such as, but not limited to, tetrahydrofuran, dimethylformamide, dimethylsulfoxide, or dioxane, at about room temperature or up to 150° C., and optionally in the presence of a catalyst such as but not limited to tetrabutylammonium iodide or sodium iodide. In certain cases, it may be beneficial to conduct this reaction in the presence of a base such as, but not limited to, triethylamine, potassium carbonate, potassium tert-butoxide or sodium hydride. The intermediate (2) can be converted to (3) by reaction with an acid chloride ($R^1$COCl) or carboxylic acid ($R^1$CO$_2$H) under appropriate conditions. For example, intermediate (2) can be reacted with $R^1$COCl in a solvent such as, but not limited to, tetrahydrofuran, dimethylformamide, or dichloromethane at a temperature from about 25° C. to about 50° C. in the presence of a base such as, but not limited to, triethylamine, diisopropylethylamine, or potassium carbonate, and optionally in the presence of a catalyst such as 4-dimethylaminopyridine. Alternatively, intermediate (2) can be reacted with $R^1$CO$_2$H in a solvent such as, but not limited to, tetrahydrofuran or dimethylformamide in the presence of a coupling reagent such as 1,1'-carbonyldiimidazole (CDI), bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), or O-benzotriazol-1-yl-N,N,N',N'-tetramethyluronium tetrafluoroborate (TBTU), in the presence or absence of a coupling auxiliary such as, but not limited to, 1-hydroxy-7-azabenzotriazole (HOAT) or 1-hydroxybenzotriazole hydrate (HOBT). The reaction is generally conducted in the presence or absence of a base such as, but not limited to, N-methyl morpholine, triethylamine, or diisopropylethylamine.

Alternatively, compounds of formula (3) can be prepared according to the general procedures as outlined in Scheme 2.

Scheme 2

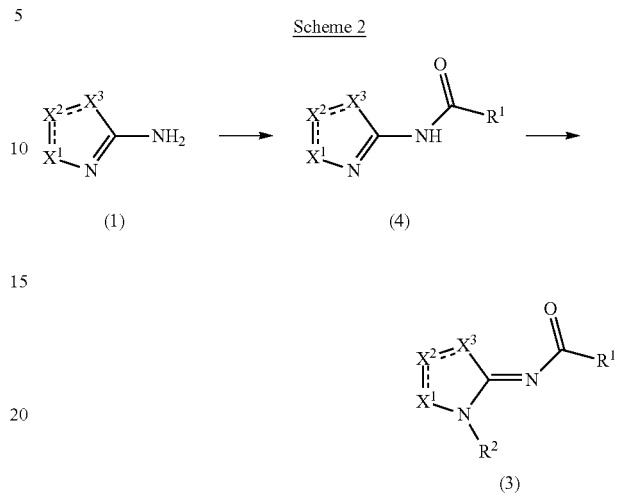

Compounds of formula (1) can be converted to intermediate (4) by reaction with $R^1$COCl or $R^1$CO$_2$H using reaction conditions as described in Scheme 1 for the transformation of (2) to (3). The intermediate (4) can be converted to (3) by reaction with $R^2$—$X^{101}$, wherein $X^{101}$ is Cl, Br, I, OTs, or OMs, using reaction conditions as described in Scheme 1 for the transformation of (1) to (2).

Scheme 3

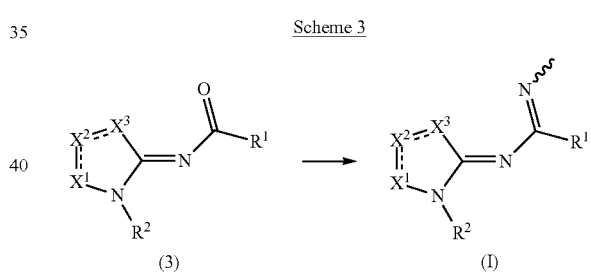

As outlined in Scheme 3, compounds of formula (3) when treated with Lawesson's reagent in toluene, at temperatures ranging from about 60° C. to about 85° C., followed by treatment with mercury (II) acetate (or other similar mercury reagents), compounds of formula Y—NH$_2$, and a base such as but not limited to triethylamine or diisopropylethylamine, and in a solvent such as dioxane or acetonitrile, can provide compounds of general formula (I).

Scheme 4

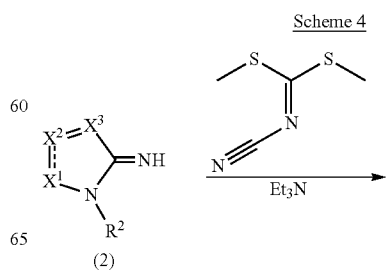

-continued

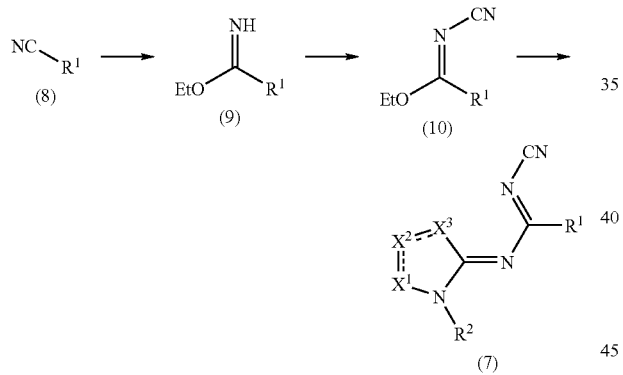

Compounds of general formula (I) wherein Y=CN as represented by formula (7) can be prepared according to the method outlined in Scheme 4. Reaction of compounds of formula (2) with commercially available dimethyl N-cyanodithioiminocarbonate in an aprotic solvent, like THF, dioxane, acetonitrile, etc. in the presence of a base, like triethylamine, N-methylmorpholine, NaH, etc., at temperatures ranging from about room temperature to about 50° C. for about 8-24 hours affords intermediates of formula (6). Reaction of the intermediates (6) with boronic acids of formula $(HO)_2B$—$R^1$ in the presence of copper carboxylates (e.g., copper acetate or copper 2-thiophenecarboxylate), a trialkylphosphite (e.g., triethylphosphite) and tris(dibenzylideneacetone)dipalladium(0) or other selected Pd(0) catalysts, in dimethoxyethane (or other aprotic solvents) at about 80-100° C. for about 12-24 hours provides the products of formula (7).

Scheme 5

Compounds of formula (7) can also be prepared using the general method shown in Scheme 5. Nitriles of formula (8) can be reacted with an alcohol (e.g., methanol or ethanol) and HCl in a solvent such as dichloromethane at about 0° C. to about room temperature to form the intermediate iminoether (9). The iminoether (9) in a solvent such as acetonitrile can be treated with a solution of sodium phosphate monobasic monohydrate, sodium phosphate dibasic heptahydrate and cyanamide in water, at about room temperature for about 12-24 hours to produce the intermediate cyanoiminoethers (10). The cyanoiminoethers (10) can be reacted with compounds of formula (2), either neat or in a solvent such as toluene, tetrahydrofuran, acetonitrile, or dimethylformamide, at temperatures from about room temperature to about 100° C. for 8-24 hours to produce compounds of formula (7).

Heteroarylamines (1) may be obtained from commercial sources or may be prepared using methods well-known to those skilled in the art. For example, heteroaryl amines of formula (1) wherein $X^1$ is nitrogen; $X^3$ is sulfur; the bond between $X^1$ and $X^2$ is a double bond; and the bond between $X^2$ and $X^3$ is a single bond; as represented by formula (12), can be prepared using the general procedure as illustrated in Scheme 6.

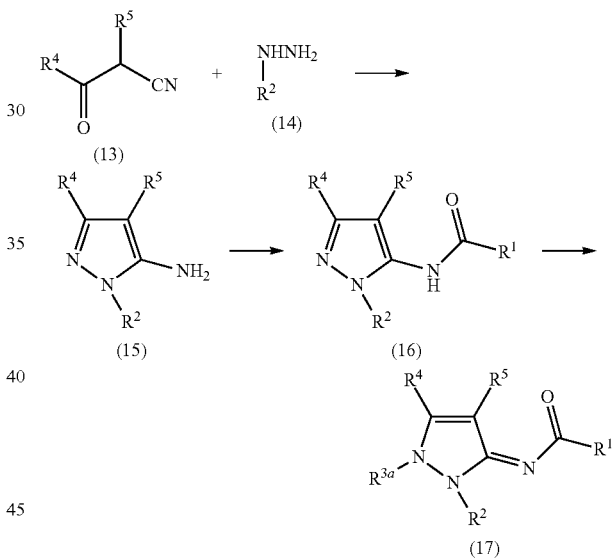

Carboxylic acids of formula (11) can be treated with thiosemicarbazide and phosphorus oxychloride at a temperature of about 90° C., in a solvent such as, but not limited to, dioxane to provide compounds of formula (12).

Intermediates of general formula (3) wherein $X^1$ is $N(R^{3a})$; $X^3$ is $CR^5$, the bond between $X^1$ and $X^2$ is a single bond; and the bond between $X^2$ and $X^3$ is a double bond, as represented by formula (17), can be synthesized using the general procedures as outlined in Scheme 7.

Hydrazines of formula (14) can be reacted with ketonitriles (13) in a solvent such as, but not limited to, ethanol, at a temperature of between about 0° C. to about 80° C., to provide intermediates of formula (15). These intermediate aminopyrazoles (15) can be treated with carboxylic acids of formula $R^1COOH$, or acid chlorides of formula $R^1COCl$ according to the methods outlined in Schemes 1 and 2 to provide pyrazoles (16). (16) can be converted to (17) by alkylation with an appropriate alkylating agent such as but not limited to a halide, mesylate, tosylate or sulfate in a solvent such as, but not limited to, tetrahydrofuran, toluene, acetonitrile or dioxane. This reaction may be conducted from about 0° C. to about 150° C. In certain cases the addition of a base may be beneficial. Examples of bases that may be used include but not limited to triethylamine, diisopropylethylamine, potassium carbonate, sodium hydride, sodium hydroxide, and lithium diisopropylamide.

Compounds of general formulas (2) and (3) wherein $X^1$ is $CR^3$; $X^3$ is O, the bond between $X^1$ and $X^2$ is a double bond;

and the bond between $X^2$ and $X^3$ is a single bond, represented respectively by formulas (20) and (21), can be synthesized using the general procedures as outlined in Scheme 8.

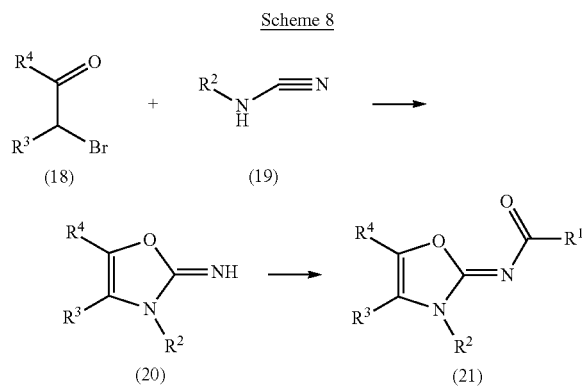

Scheme 8

Compounds of formula (18) when treated with compounds of formula (19) in the presence of potassium carbonate or sodium carbonate and in a solvent such as, but not limited to, methyl ethyl ketone, at a temperature from about 25° C. to about 100° C. can provide compounds of formula (20). Compounds of formula (20) can be converted to compounds of formula (21) by reaction with $R^1COCl$ or $R^1CO_2H$ using reaction conditions as described in Scheme 1.

Compounds of formula (19) can be obtained from the reaction of amines of formula $R^2NH_2$ with cyanogen bromide in the presence of sodium carbonate or potassium carbonate in a solvent such as, but not limited to, ether, and at a temperature from about −25° C. to about 0° C.

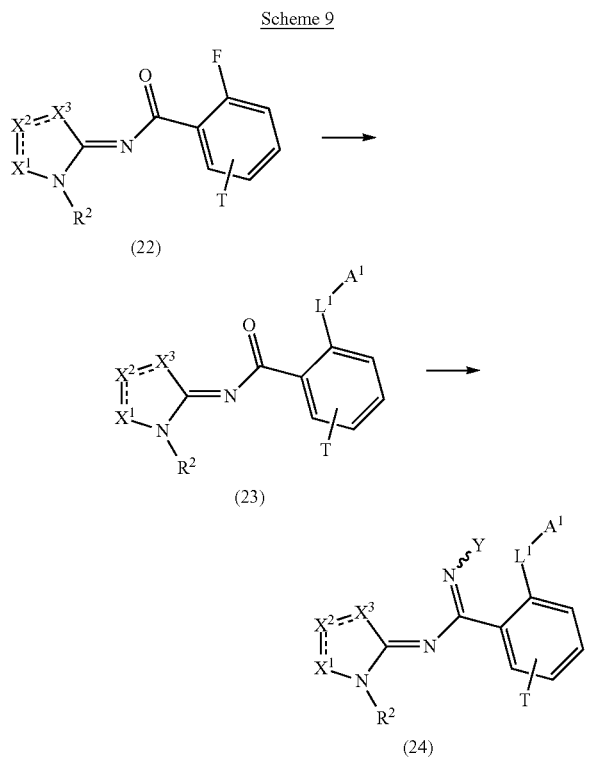

Scheme 9

Intermediates of formula (3) wherein $R^1$ is an ortho-fluoro substituted phenyl that is optionally substituted by 1, 2, 3, or 4 substituents T, represented by formula (22), can be converted to compounds of formula (23) by reaction with a group $H-L^1-A^1$, in a solvent such as, but not limited to, tetrahydrofuran, dioxane, or DMF, in the presence of a base such as, but not limited to, triethylamine, potassium tert-butoxide, or sodium hydride, at a temperature between about 0° C. and about 150° C., and optionally with microwave irradiation. Compounds of formula (23) can be converted to compounds of the invention having formula (24) using the conditions described in Scheme 3.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

g. EXAMPLES

Example 1

N-[(3E)-2-butyl-5-tert-butylisoxazol-3(2H)-ylidene]-5-chloro-N'-cyano-2-methoxybenzenecarboximidamide

Example 1A 5-tert-butyl-2-butylisoxazol-3(2H)-imine

A mixture of 5-tert-butylisoxazol-3-amine (3.0 g, 21 mmol) and 1-bromobutane (3.5 mL, 32 mmol) was warmed to 85° C. and was allowed to stir for 70 h. The mixture was cooled to ambient temperature and was purified by column chromatography (silica gel, 60% hexanes/EtOAc) to give the title compound (4.2 g, 21 mmol, 99% yield). MS (DCI/NH$_3$) m/z 197 (M+H)$^+$.

Example 1B

Methyl N-5-tert-butyl-2-butylisoxazol-3(2H)-ylidene-N'-cyanocarbamimidothioate

To a solution of the product of Example 1A (2.0 g, 10 mmol) in acetonitrile (75 mL) was added triethylamine (1.4 mL, 10 mmol) followed by dimethyl cyanocarbonimidodithioate (1.4 g, 9.3 mmol). This mixture was warmed to 50° C. and was allowed to stir for 20 h. The mixture was cooled to ambient temperature, concentrated under reduced pressure and purified by column chromatography (silica gel, 60% hexanes/EtOAc) to provide the title compound (1.4 g, 4.7 mmol, 46% yield). MS (DCI/NH$_3$) m/z 295 (M+H)$^+$.

Example 1C

N-[(3E)-2-butyl-5-tert-butylisoxazol-3(2H)-ylidene]-5-chloro-N'-cyano-2-methoxybenzenecarboximidamide To a mixture of the product of Example 1B (1.2 g, 4.1 mmol), 5-chloro-2-methoxyphenylboronic acid (1.7 g, 9.4 mmol), and copper(I) acetate (1.6 g, 13.5 mmol) in ethylene glycol dimethylether (40 mL) was added Pd$_2$dba$_3$ (0.75 g, 0.815 mmol). Triethyl phosphite (0.21 mL, 1.2 mmol) was added and the mixture was warmed to reflux and was allowed to stir for 18 h. The mixture was cooled to ambient temperature, and filtered through Celite. The filtrate was concentrated under reduced pressure. The crude material was purified by column chromatography (silica gel, 50% hexanes/EtOAc) to give the title compound (0.14 g, 0.36 mmol, 9% yield). $^1$H NMR (CDCl$_3$, 300 MHz) δ ppm 0.97 (t, J=7.1 Hz, 3H), 1.30-1.42 (m, 2H), 1.37 (s, 9H), 1.75-1.87 (m, 2H), 3.90 (s, 3H), 4.26 (t, J=6.9 Hz, 2H), 6.88-6.94 (m, 1H), 7.04-7.16 (m, 1H), 7.28-7.35 (m, 2H); MS (DCI/NH$_3$) m/z 389 (M+H)$^+$; Anal. (C$_{20}$H$_{25}$ClN$_4$O$_2$) Calc: C, 61.77; H, 6.48; N, 14.41. Found: C, 61.64; H, 6.33; N, 14.25.

Example 2

N-[(3E)-5-tert-butyl-2-isobutylisoxazol-3(2H)-ylidene]-5-chloro-N'-cyano-2-methoxybenzenecarboximidamide

Example 2A 5-tert-butyl-2-isobutylisoxazol-3(2H)-imine

A mixture of 5-tert-butylisoxazol-3-amine (3.0 g, 21 mmol) and 1-bromo-2-methylpropane (3.5 mL, 32 mmol) was warmed to 85° C. and was allowed to stir for 70 h. The mixture was cooled to ambient temperature and was purified by column chromatography (silica gel, 60% hexanes/EtOAc) to give the title compound (2.5 g, 13 mmol, 60% yield). MS (DCI/NH$_3$) m/z 197 (M+H)$^+$.

Example 2B

Methyl N-5-tert-butyl-2-isobutylisoxazol-3(2H)-ylidene-N'-cyanocarbamimidothioate To a solution of the product of Example 2A (2.0 g, 10 mmol) in acetonitrile (75 mL) was added triethylamine (1.5 mL, 11 mmol) followed by dimethyl cyanocarbonimidodithioate (1.4 g, 9.4 mmol). This mixture was warmed to 50° C. and was allowed to stir for 20 h. The mixture was cooled to ambient temperature, concentrated under reduced pressure and purified by column chromatography (silica gel, 60% hexanes/EtOAc) to provide the title compound (1.6 g, 5.6 mmol, 55% yield). MS (DCI/NH$_3$) m/z 295 (M+H)$^+$.

Example 2C

N-[(3E)-5-tert-butyl-2-isobutylisoxazol-3(2H)-ylidene]-5-chloro-N'-cyano-2-methoxybenzenecarboximidamide To a mixture of the product of Example 2B (0.82 g, 2.8 mmol), 5-chloro-2-methoxyphenylboronic acid (1.2 g, 6.4 mmol), and copper(I)acetate (1.1 g, 9.2 mmol) in ethylene glycol dimethylether (25 mL) was added Pd$_2$dba$_3$ (0.51 g, 0.56 mmol). This mixture was degassed three times with a N$_2$ back-flush each time. Triethyl phosphite (0.21 mL, 1.2 mmol) was added and the mixture was warmed to reflux and was allowed to stir for 18 h. The mixture was cooled to ambient temperature, filtered through Celite and the filtrate was concentrated under reduced pressure. The crude material was purified by column chromatography (silica gel, 50% hexanes/EtOAc) to give the title compound (0.18 g, 0.46 mmol, 17% yield). $^1$H NMR (CDCl$_3$, 300 MHz) δ ppm 0.98 (d, J=6.7 Hz, 6H), 1.37 (s, 9H), 2.13-2.35 (m, 1H), 3.90 (s, 3H), 4.11 (dd, J=8.7, 7.1 Hz, 2H), 6.91 (d, J=8.7 Hz, 1H), 7.08-7.21 (m, 1H), 7.27-7.35 (m, 2H)); MS (DCI/NH$_3$) m/z 389 (M+H)$^+$; Anal. (C$_{20}$H$_{25}$ClN$_4$O$_2$.0.15C$_4$H$_8$O$_2$) Calc: C, 61.53; H, 6.57; N, 13.93. Found: C, 61.59; H, 6.50; N, 13.62.

Example 3

N-[(3E)-5-tert-butyl-2-isobutylisoxazol-3(2H)-ylidene]-N'-cyano-2-ethoxy-5-(trifluoromethyl)benzenecarboximidamide To a mixture of the product of Example 2B (0.50 g, 1.7 mmol), 2-ethoxy-5-(trifluoromethyl)phenylboronic acid (0.91 g, 3.9 mmol), and copper(I)acetate (0.69 g, 5.6 mmol) in ethylene glycol dimethylether (10 mL) was added Pd$_2$dba$_3$ (0.31 g, 0.34 mmol). This mixture was degassed three times with a N$_2$ back-flush each time. Triethyl phosphite (0.21 mL, 1.2 mmol) was added and the mixture was warmed to reflux and was allowed to stir for 18 h. The mixture was cooled to ambient temperature, filtered through Celite and the filtrate was concentrated under reduced pressure. The crude material was purified by column chromatography (silica gel, 50% hexanes/EtOAc) to give the title compound (90 mg, 0.21 mmol, 12% yield). $^1$H NMR (CDCl$_3$, 300 MHz) δ ppm 0.98 (d, J=6.8 Hz, 6H), 1.38 (s, 9H), 1.48 (t, J=7.0 Hz, 3H), 2.15-2.33 (m, 1H), 4.09 (d, J=7.1 Hz, 2H), 4.21 (q, J=7.1 Hz, 2H), 7.03 (d, J=8.1 Hz, 1H), 7.06-7.19 (m, 1H), 7.56-7.63 (m, 2H); MS (DCI/NH$_3$) m/z 437 (M+H)$^+$; Anal. (C$_{22}$H$_{27}$F$_3$N$_4$O$_2$) Calc: C, 60.54; H, 6.24; N, 12.84. Found: C, 60.70; H, 5.95; N, 12.99.

Example 4

N-[(2Z)-3-butyl-5-tert-butyl-1,3,4-thiadiazol-2(3H)-ylidene]-5-chloro-N'-cyano-2-methoxybenzenecarboximidamide

Example 4A

N-(5-tert-butyl-1,3,4-thiadiazol-2-yl)-5-chloro-2-methoxybenzamide

To a solution of 5-tert-butyl-1,3,4-thiadiazol-2-amine (1.57 g, 10 mmol) and 5-chloro-2-methoxybenzoyl chloride (2.05 g, 10 mmol) in CH$_2$Cl$_2$ (45 mL) at 0° C. was added dropwise triethylamine (1.7 mL, 12 mmol). The reaction mixture was allowed to warm to ambient temperature and stirred for 12 hours. The mixture was then washed with water, brine, dried with MgSO$_4$, filtered, and concentrated under reduced pressure to afford 3.2 g of the title compound. $^1$H NMR (300 MHz, DMSO-D$_6$) δ ppm 1.43 (s, 9H), 3.88 (s, 3H), 7.22 (d, J=8.8 Hz, 1H), 7.45-7.76 (m, 2H), 12.43 (s, 1H). MS (DCI/NH$_3$) m/z 326 (M+H)$^+$.

Example 4B

N-[(2Z)-3-butyl-5-tert-butyl-1,3,4-thiadiazol-2(3H)-ylidene]-5-chloro-2-methoxybenzamide A mixture of the product from Example 4A (325 mg, 1 mmol), 1-iodobutane (551 mg, 3 mmol) and potassium carbonate (276 mg, 2 mmol) in toluene (25 mL) was treated with tetrabutylammonium iodide (11 mg, 0.03 mmol), tetrabutylammonium hydrogen sulfate (10 mg, 0.03 mmol), and tetraethylammonium iodide (11 mg, 0.04 mmol) and the resulting mixture was refluxed for 8 h. The mixture was washed with water, brine, dried with MgSO$_4$, filtered, and concentrated under reduced pressure. The residue was purified by chromatography (hexane-EtOAc 2:1) to afford 360 mg of the title compound. $^1$H NMR (300 MHz, DMSO-D$_6$) δ ppm 0.92 (t, J=7.3 Hz, 3H), 1.29-1.47 (m, 11H), 1.73-1.88 (m, 2H), 3.77-3.83 (m, 3H), 4.34 (t, J=6.9 Hz, 2H), 7.14 (d, J=9.1 Hz, 1H), 7.50 (dd, J=8.7, 2.8 Hz, 1H), 7.74 (d, J=2.8 Hz, 1H). MS (DCI/NH$_3$) m/z 382 (M+H)$^+$.

Example 4C

N-[(2Z)-3-butyl-5-tert-butyl-1,3,4-thiadiazol-2(3H)-ylidene]-5-chloro-2-methoxybenzenecarbothioamide A mixture of product from Example 4B (350 mg, 0.92 mmol) and Lawesson's Reagent (371 mg, 0.92 mg) in toluene (30 mL) was refluxed for 40 min at 80° C. The mixture was cooled to room temperature and purified by chromatography (hexane-EtOAc 2:1) to afford 270 mg of the title compound. $^1$H NMR (300 MHz, DMSO-D$_6$) δ ppm 0.88 (t, 3H), 1.23-1.34 (m, 2H), 1.38-1.45 (s, 9H), 1.75-1.89 (m, 2H), 3.72-3.79 (s, 3H), 4.46 (t, 2H), 7.05-7.14 (m, 1H), 7.37-7.46 (m, 2H). MS (DCI/NH$_3$) m/z 398 (M+H)$^+$.

Example 4D

N-[(2Z)-3-butyl-5-tert-butyl-1,3,4-thiadiazol-2(3H)-ylidene]-5-chloro-N'-cyano-2-methoxybenzenecarboximidamide To a solution of product from Example 4C (165 mg, 0.42 mmol), cyanamide (42 mg, 1 mmol) and triethylamine (0.07 mL, 0.5 mmol) in acetonitrile (20 mL) was added mercuric acetate (143 mg, 0.45 mmol) and the resulting mixture was refluxed at 80° C. for 45 min. The solvent was removed under reduced pressure and the residue was purified by chromatography (hexane-EtOAc 1:1) to afford 150 mg of the title compound. $^1$H NMR (300 MHz, DMSO-D$_6$) δ ppm 0.89 (t, J=7.3 Hz, 3H), 1.24-1.32 (m, 2H), 1.42 (s, 9H), 1.74-1.85 (m, 2H), 3.83 (s, 3H), 4.37 (t, J=7.0 Hz, 2H), 7.23 (d, J=8.8 Hz, 1H), 7.40 (d, J=2.7 Hz, 1H), 7.55 (dd, J=8.8, 2.7 Hz, 1H). MS (DCI/NH$^3$) m/z 406 (M+H)$^+$. Anal. calculated for C$_{19}$H$_{24}$ClN$_5$OS: C, 56.22 H, 5.96 N, 17.25. Found: C, 56.08 H, 5.99 N, 16.85.

Example 5

N-[(2Z)-5-tert-butyl-3-isobutyl-1,3,4-thiadiazol-2(3H)-ylidene]-5-chloro-N'-cyano-2-methoxybenzenecarboximidamide

Example 5A

N-[(2Z)-5-tert-butyl-3-(2-methylpropyl)-1,3,4-thiadiazol-2(3H)-ylidene]-5-chloro-2-methoxybenzamide The product of Example 4A (325 mg, 1 mmol) and 1-iodo-2-methylpropane (920 mg, 5 mmol) were processed using the method described in Example 4B to afford the title compound. $^1$H NMR (300 MHz, DMSO-D$_6$) δ ppm 0.90 (d, 6H), 1.39 (s, 9H), 2.25-2.36 (m, 1H), 3.76-3.83 (m, 3H), 4.17 (d, J=7.1 Hz, 2H), 7.14 (d, J=8.8 Hz, 1H), 7.51 (d, J=2.7 Hz, 1H), 7.71 (d, J=3.1 Hz, 1H). MS (DCI/NH$_3$) m/z 382 (M+H)$^+$. Anal. calculated for C$_{18}$H$_{24}$ClN$_3$OS: C, 56.61; H, 6.33; N, 11.00. Found: C, 56.84; H, 6.43; N, 10.77.

Example 5B

N-[(2Z)-5-tert-butyl-3-(2-methylpropyl)-1,3,4-thiadiazol-2(3H)-ylidene]-5-chloro-2-methoxybenzenecarbothioamide The product of Example 5A (320 mg, 0.84 mmol) and Lawesson's Reagent (339 mg, 0.84 mmol) were processed using the method described in Example 4C to afford the title compound. $^1$H NMR (300 MHz, DMSO-D$_6$) δ ppm 0.89 (d, 6H), 1.41-1.47 (m, 9H), 2.27-2.37 (m, 1H), 3.75 (s, 3H), 4.29 (d, J=7.5 Hz, 2H), 7.10 (d, J=9.2 Hz, 1H), 7.36-7.43 (m, 2H). MS (DCI/NH$_3$) m/z 398 (M+H)$^+$. Anal. Calculated for C$_{18}$H$_{24}$ClN$_3$OS$_2$: C, 54.32 H, 6.08 N, 10.56. Found: C, 54.60; H, 6.10; N, 10.36.

Example 5C

N-[(2Z)-5-tert-butyl-3-isobutyl-1,3,4-thiadiazol-2 (3H)-ylidene]-5-chloro-N'-cyano-2-methoxybenzenecarboximidamide The product of Example 5B (280 mg, 0.71 mmol) and cyanoamide (106 mg, 2.5 mmol) were processed using the method described in Example 4D to afford the title compound. $^1$H NMR (300 MHz, DMSO-D$_6$) δ ppm 0.89 (d, 6H), 1.42 (s, 9H), 2.20-2.32 (m, 1H), 3.82 (s, 3H), 4.21 (d, J=7.1 Hz, 2H), 7.23 (d, J=9.2 Hz, 1H), 7.38 (d, J=2.7 Hz, 1H), 7.56 (dd, 1H). MS (DCI/NH$_3$) m/z 406 (M+H)$^+$. Anal. calculated for C$_{19}$H$_{24}$ClN$_5$OS: C, 56.22; H, 5.96; N, 17.25. Found: C, 56.27; H, 5.95; N, 17.02.

Example 6

N-{(3E)-5-tert-butyl-1-methyl-2-[(2R)-tetrahydrofuran-2-ylmethyl]-1,2-dihydro-3H-pyrazol-3-ylidene}-N'-cyano-2-fluoro-3-(trifluoromethyl)benzenecarboximidamide

Example 6A

(R)-((tetrahydrofuran-2-yl)methyl)hydrazine dihydrochloride

To (R)-(tetrahydrofuran-2-yl)methanol (4.0 g, 39.2 mmol), di-tert-butyl hydrazine-1,2-dicarboxylate (3.64 g, 15.67 mmol) and triphenylphosphine (15.41 g, 58.7 mmol) in THF (100 mL) was added (E)-di-tert-butyl diazene-1,2-dicarboxylate (13.5 g, 5.87 mmol). The mixture was stirred at ambient temperature for 3 h then diluted with water and extracted with EtOAc (100 mL×2). The organic extract was washed with brine and concentrated. Purification by flash chromatography (silica gel, 5-30% EtOAc/hexane) afforded 10.2 g (82%) of (R)-di-tert-butyl 1-((tetrahydrofuran-2-yl)-methyl)-hydrazine-1,2-dicarboxylate, which was dissolved in a solution of 4M HCl in dioxane (40 mL) and stirred at ambient temperature overnight. The solvent was removed under reduced pressure and ethyl acetate (20 mL) was added with stirring. The solid precipitate was filtered, washed with ether (10 mL) and dried in vacuum to yield 7.8 g (97%) of the title compound as a white solid. $^1$H NMR (300 MHz, DMSO-d$_6$) δ ppm 1.48-1.63 (m, 1H), 1.73-1.88 (m, 2H), 1.90-2.02 (m, 1H), 2.84-3.01 (m, 2H), 3.61-3.71 (m, 1H), 3.72-3.83 (m, 1H), 3.97-4.08 (m, 1H), 5.76 (br, 5H); MS (ESI) m/z 117 (M+H)$^+$.

Example 6B

(R)-3-tert-butyl-1-((tetrahydrofuran-2-yl)methyl)-1H-pyrazol-5-amine hydrochloride A mixture of Example 6A (7.8 g, 41.3 mmol) and 4,4-dimethyl-3-oxopentanenitrile (5.68 g, 45.4 mmol) in ethanol (50 mL) was refluxed at 90° C. for 6 h, then the solvent was removed under reduced pressure and ethyl acetate (10 mL) was added with stirring. The white solid that precipitated was filtered, washed with ether and dried to yield 10.4 g (97%) of the title compound. $^1$H NMR (300 MHz, DMSO-d$_6$) δ ppm 1.14 (s, 9H), 1.60-1.97 (m, 4H), 3.50-3.66 (m, 1H), 3.67-3.79 (m, 1H), 3.83 (d, J=5.16 Hz, 2H), 3.99-4.16 (m, 1H), 4.85 (s, 2H), 5.15 (s, 1H); MS (ESI) m/z 224 (M+H)$^+$, 222 (M–H)$^-$.

Example 6C

(R)—N-(3-tert-butyl-1-((tetrahydrofuran-2-yl)methyl)-1H-pyrazol-5-yl)-2-fluoro-3-(trifluoromethyl) benzamide To the mixture of Example 6B (293 mg, 1.129 mmol) and triethylamine (0.472 mL, 3.39 mmol) in CH$_2$Cl$_2$ (5 mL) cooled with an ice-bath was added 2-fluoro-3-(trifluoromethyl)benzoyl chloride (307 mg, 1.355 mmol) in one portion. The mixture was stirred at ambient temperature for 2 h, the solvent removed under reduced pressure and the residue purified by flash chromatography (silica gel, 10-60% EtOAc/hexane) to yield 420 mg (90%) of the title compound. $^1$H NMR (300 MHz, DMSO-d$_6$) δ ppm 1.24 (s, 9H), 1.58-1.97 (m, 4H), 3.55-3.78 (m, 2H), 4.06-4.20 (m, 3H), 6.30 (s, 1H), 7.57 (t, J=7.80 Hz, 1H), 8.01 (q, J=8.02 Hz, 2H), 10.42 (s, 1H); MS (ESI) m/z 414 (M+H)$^+$, 412 (M–H)$^-$.

Example 6D

N-{(3E)-5-tert-butyl-1-methyl-2-[(2R)-tetrahydrofuran-2-ylmethyl]-1,2-dihydro-3H-pyrazol-3-ylidene}-2-fluoro-3-(trifluoromethyl)benzamide A mixture of Example 6C (400 mg, 0.97 mmol) and dimethyl sulfate (0.37 mL, 3.88 mmol) in toluene (2 mL) was heated in a microwave reactor (300 W, CEM Explorer®) at 150° C. for 1 hour. The solvent was removed under reduced pressure and the residue was purified by flash chromatography (silica gel; solvent A=EtOAc/MeOH/Et$_3$N (90:10:0.5); solvent B=hexane in 10-60% gradient A/B) to yield 331.5 mg (80%) of the title compound. $^1$H NMR (300 MHz, DMSO-d$_6$) δ ppm 1.44 (s, 9H), 1.50-1.67 (m, 1H), 1.75-1.96 (m, 2H), 1.99-2.14 (m, 1H), 3.64-3.84 (m, 2H), 4.12 (s, 3H), 4.18-4.26 (m, 1H), 4.55-4.77 (m, 2H), 6.98 (s, 1H), 7.63 (t, J=7.73 Hz, 1H), 8.00-8.13 (m, 2H); MS (ESI) m/z 428 (M+1H).

Example 6E

N-{(3E)-5-tert-butyl-1-methyl-2-[(2R)-tetrahydrofuran-2-ylmethyl]-1,2-dihydro-3H-pyrazol-3-ylidene}-2-fluoro-3-(trifluoromethyl)benzenecarbothioamide To Example 6D (138 mg, 0.323 mmol) in toluene (10 mL) was added Lawesson's Reagent (131 mg, 0.323 mmol). The mixture was refluxed at 110° C. for 2 h, the solvent removed and the residue purified by chromatography (silica gel; solvent A=EtOAc/MeOH/Et$_3$N (90/10/0.2); solvent B=hexane in 5-60% gradient A/B) to yield 90 mg (63%) of the title compound. $^1$H NMR (300 MHz, DMSO-d$_6$) δ ppm 1.37-1.44 (m, 9H), 1.59-1.92 (m, 4H), 3.57-3.79 (m, 2H), 4.04 (s, 3H), 4.11-4.20 (m, 1H), 4.33-4.44 (m, 2H), 7.31 (t, J=7.73 Hz, 1H), 7.55-7.65 (m, 1H), 7.59 (s, 1H), 7.81-7.90 (m, 1H), 8.25 (s, 1H). MS (ESI) m/z 444 (M+H)$^+$, 442 (M–H)$^-$.

Example 6F

N-{(3E)-5-tert-butyl-1-methyl-2-[(2R)-tetrahydrofuran-2-ylmethyl]-1,2-dihydro-3H-pyrazol-3-ylidene}-N'-cyano-2-fluoro-3-(trifluoromethyl)benzenecarboximidamide To example 6E (82 mg, 0.185 mmol) in acetonitrile (8 mL) was added triethylamine (77 µL, 0.555 mmol), cyanamide (15.55 mg, 0.370 mmol) and mercuric acetate (77 mg, 0.240 mmol). The mixture was refluxed for 2 h, then filtered and concentrated. Purification by reverse phase preparative HPLC on a Waters Symmetry C8 column (25 mm×100 mm, 7 μm particle size) using a gradient of 10% to 100% acetonitrile: 10 mM ammonium acetate over 8 minutes (10 minutes run time) at a flow rate of 40 mL/minute afforded 43 mg (51.5%) of the title compound. $^1$H NMR (300 MHz, DMSO-$d_6$) δ ppm 1.33-1.46 (m, 9H), 1.55-1.68 (m, 1H), 1.68-1.82 (m, 2H), 1.82-1.95 (m, 1H), 3.56-3.78 (m, 2H), 4.00 (s, 3H), 4.08-4.19 (m, 1H), 4.32-4.48 (m, 2H), 6.72 (s, 1H), 7.48 (t, J=7.80 Hz, 1H), 7.70-7.88 (m, 2H); MS (ESI) m/z 452 (M+H)$^+$, 450(M−H)$^-$.

Example 7

N-[(2Z)-5-tert-butyl-3-(1,3-thiazol-4-ylmethyl)-1,3, 4-thiadiazol-2(3H)-ylidene]-5-chloro-N'-cyano-2-methoxybenzenecarboximidamide Example 7A N-(5-tert-butyl-1,3,4-thiadiazol-2-yl)-5-chloro-2-methoxybenzamide To a solution of 5-tert-butyl-1,3,4-thiadiazol-2-amine (1.57 g, 10 mmol) and 5-chloro-2-methoxybenzoyl chloride (2.05 g, 10 mmol) in $CH_2Cl_2$ (45 mL) at 0° C. was added dropwise triethylamine (1.7 mL, 12 mmol) and the reaction mixture was allowed to warm to ambient temperature for 12 h. The mixture was then washed with water, brine, dried with $MgSO_4$, filtered, and concentrated under reduced pressure to afford 3.2 g of the title compound. $^1$H NMR (300 MHz, DMSO-$D_6$) δ ppm 1.43 (s, 9H), 3.88 (s, 3H), 7.22 (d, J=8.8 Hz, 1H), 7.45-7.76 (m, 2H), 12.43 (s, 1H). MS (DCI/NH$_3$) m/z 326 (M+H)$^+$.

Example 7B

N-[(2Z)-5-tert-butyl-3-(1,3-thiazol-4-ylmethyl)-1,3, 4-thiadiazol-2(3H)-ylidene]-5-chloro-2-methoxybenzamide A mixture of product from Example 7A (489 mg, 1.5 mmol), 4-(chloromethyl)thiazole (200 mg, 1.5 mmol) and potassium carbonate (415 mg, 3 mmol) in toluene (25 mL) was treated with tetrabutylammonium iodide (11 mg, 0.03 mmol), tetrabutylammonium hydrogen sulfate (10 mg, 0.03 mmol) and tetraethylammonium iodide (11 mg, 0.04 mmol) and the resulting mixture was refluxed for 8 h. The mixture was washed with water, brine, dried with $MgSO_4$, filtered, and concentrated under reduced pressure. The residue was purified by chromatography (hexane-EtOAc 2:1) to afford 300 mg of the title compound. $^1$H NMR (300 MHz, DMSO-D6) δ ppm 1.37 (s, 9H), 3.78 (s, 3H), 5.69 (s, 2H), 7.13 (d, J=9.2 Hz, 1H), 7.49 (dd, J=8.8, 2.7 Hz, 1H), 7.61 (d, J=2.0 Hz, 1H), 7.71 (d, J=3.1 Hz, 1H), 9.08 (d, J=2.0 Hz, 1H). MS (DCI/NH$_3$) m/z 423 (M+H)$^+$.

Example 7C

N-[(2Z)-5-tert-butyl-3-(1,3-thiazol-4-ylmethyl)-1,3, 4-thiadiazol-2(3H)-ylidene]-5-chloro-2-methoxybenzenecarbothioamide To a solution of product from Example 7B (280 mg, 0.66 mmol) in toluene (15 mL) was added Lawesson's reagent (268 mg, 0.66 mmol) and the reaction mixture was refluxed at 80° C. for 45 min. After cooling to room temperature, the mixture was diluted with EtOAc, washed with a 10% solution of sodium bicarbonate, brine and dried with anhydrous $MgSO_4$. Purification by column chromatography (1:1 Hexane-EtOAc) provided 260 mg (89%) of the title compound. $^1$H NMR (300 MHz, CDCl$_3$) δ ppm 1.46 (s, 9H), 3.78 (s, 3H), 5.84 (s, 2H), 6.87 (d, J=8.8 Hz, 1H), 7.21-7.31 (m, 1H), 7.34 (d, J=2.0 Hz, 1H), 7.51 (d, J=2.7 Hz, 1H), 8.78 (d, J=2.0 Hz, 1H). MS (DCI/NH$_3$) m/z 440 (M+H)$^+$. Anal. Calculated for $C_{18}H_{19}ClN_4OS_3$: C, 49.24; H, 4.36; N, 12.76. Found: C, 49.09; H, 4.37; N, 12.25.

Example 7D

N-[(2Z)-5-tert-butyl-3-(1,3-thiazol-4-ylmethyl)-1,3, 4-thiadiazol-2(3H)-ylidene]-5-chloro-N'-cyano-2-methoxybenzenecarboximidamide To a solution of product from Example 7C (223 mg, 0.508 mmol), cyanamide (107 mg, 2.5 mmol) and triethylamine (0.28 mL, 2.0 mmol) in acetonitrile (20 mL) was added mercuric acetate (318 mg, 2.2 mmol) and the resulting mixture was refluxed at 80° C. for 24 hours. The solvent was removed under reduced pressure and the residue was purified by chromatography (hexane-EtOAc 1:1) to afford 150 mg of the title compound. $^1$H NMR (300 MHz, DMSO-D$_6$) δ ppm 1.36-1.45 (m, 9H), 3.82 (s, 3H), 5.73 (s, 2H), 7.22 (d, J=8.8 Hz, 1H), 7.28-7.35 (m, J=2.7 Hz, 1H), 7.55 (dd, J=8.8, 2.7 Hz, 1H), 7.64 (d, J=2.0 Hz, 1H), 9.08 (d, J=2.0 Hz, 1H). MS (DCI/NH$_3$) m/z 447 (M+H)$^+$. Anal. Calculated for $C_{18}H_{21}ClN_4OS_2$: C, 52.86; H, 5.18; N, 13.70. Found: C, 52.67; H, 5.14; N, 13.40.

Example 8

N-[(2Z)-5-tert-butyl-3-(3-cyanopropyl)-1,3,4-thiadiazol-2(3H)-ylidene]-5-chloro-N'-cyano-2-methoxybenzenecarboximidamide Example 8A N-[(2Z)-5-tert-butyl-3-(3-cyanopropyl)-1,3,4-thiadiazol-2(3H)-ylidene]-5-chloro-2-methoxybenzamide A mixture of product from Example 7A (645 mg, 2 mmol), 4-bromobutanenitrile (0.4 mL, 4 mmol) and potassium carbonate (547 mg, 4 mmol) in toluene (35 mL) was treated with tetrabutylammonium iodide (11 mg, 0.03 mmol), tetrabutylammonium hydrogen sulfate (10 mg, 0.03 mmol) and tetraethylammonium iodide (11 mg, 0.04 mmol) and the resulting mixture was refluxed for 8 h. The mixture was washed with water, brine, dried with $MgSO_4$, filtered, and concentrated under reduced pressure. The residue was purified by chromatography (hexane-EtOAc 2:1) to afford 600 mg (77%) of the title compound. $^1$H NMR (300 MHz, DMSO-D$_6$) δ ppm 1.39 (s, 9H), 2.06-2.24 (m, 2H), 2.60 (t, J=7.0 Hz, 2H), 3.77-3.84 (m, 3H), 4.43 (t, J=6.6 Hz, 2H), 7.14 (d, J=8.8 Hz, 1H), 7.50 (dd, J=8.8, 3.1 Hz, 1H), 7.77 (d, J=2.7 Hz, 1H). MS (DCI/NH$_3$) 393 m/z (M+H)$^+$.

Example 8B

N-[(2Z)-5-tert-butyl-3-(3-cyanopropyl)-1,3,4-thiadiazol-2(3H)-ylidene]-5-chloro-2-methoxybenzenecarbothioamide To a solution of product from Example 8A (580 mg, 1.47 mmol) in toluene (15 mL) was added Lawesson's reagent (597 mg, 1.47 mmol) and the reaction mixture was refluxed at 80° C. for 45 min. After cooling to room temperature, the mixture was diluted with EtOAc, washed with a 10% solution of sodium bicarbonate, brine and dried with anhydrous MgSO$_4$. Purification by column chromatography (1:1 Hexane-EtOAc) provided 470 mg (77%) of the title compound. $^1$H NMR (300 MHz, CDCl$_3$) δ ppm 1.46 (s, 9H), 3.78 (s, 3H), 5.84 (s, 2H), 6.87 (d, J=8.8 Hz, 1H), 7.22-7.32 (m, 1H), 7.34 (d, J=2.0 Hz, 1H), 7.51 (d, J=2.7 Hz, 1H), 8.78 (d, J=2.0 Hz, 1H). MS (DCI/NH$_3$) 409 m/z (M+H)$^+$.

Example 8C

N-[(2Z)-5-tert-butyl-3-(3-cyanopropyl)-1,3,4-thiadiazol-2(3H)-ylidene]-5-chloro-2-methoxybenzamide To a solution of product from Example 8B (440 mg, 1 mmol), cyanamide (226 mg, 5 mmol) and triethylamine (0.6 mL, 4.3 mmol) in acetonitrile (20 mL) was added mercuric acetate (754 mg, 2.3 mmol) and the resulting mixture was refluxed at 80° C. for 24 hours. The solvent was removed under reduced pressure and the residue was purified by chromatography (hexane-EtOAc 1:1) to afford 168 mg of the title compound. $^1$H NMR (300 MHz, DMSO-D$_6$) δ ppm 1.34-1.44 (m, 9H), 2.08-2.22 (m, 2H), 2.60 (t, J=7.0 Hz, 2H), 3.80 (s, 3H), 4.43 (t, J=6.6 Hz, 2H), 7.14 (d, J=8.8 Hz, 1H), 7.51 (dd, J=8.8, 2.7 Hz, 1H), 7.77 (d, J=3.1 Hz, 1H). MS (DCI/NH$_3$) 417 m/z (M+H)$^+$. Anal. calculated for C$_{19}$H$_{21}$ClN$_6$OS: C, 54.73; H, 5.08; N, 20.16. Found: C, 54.63; H, 5.35; N, 20.03.

Example 9

N-[(2Z)-3-butyl-5-tert-butyl-1,3,4-thiadiazol-2(3H)-ylidene]-5-chloro-N',2-dimethoxybenzenecarboximidamide The product of Example 4C (80 mg, 0.2 mmol) and O-methylhydroxylamine (47 mg, 1.0 mmol) were processed using the method described in Example 4D to afford the title compound. $^1$H NMR (300 MHz, DMSO-D$_6$) δ ppm 0.86 (t, J=7.3 Hz, 3H), 1.19-1.27 (m, 2H), 1.31-1.39 (m, 9H), 1.62-1.75 (m, 2H), 3.66-3.77 (m, 6H), 4.06 (t, J=7.0 Hz, 2H), 7.02-7.13 (m, 2H), 7.38 (dd, J=8.8, 2.7 Hz, 1H). MS (DCI/NH$_3$) m/z 411 (M+H)$^+$.

Example 10

N-{(3E)-5-tert-butyl-1-methyl-2-[(2R)-tetrahydrofuran-2-ylmethyl]-1,2-dihydro-3H-pyrazol-3-ylidene}-N'-cyano-2-(2-fluoroethoxy)-5-(trifluoromethyl)benzenecarboximidamide Example 10A (R)-di-tert-butyl 1-((tetrahydrofuran-2-yl)methyl)hydrazine-1,2-dicarboxylate To a mixture of (R)-(tetrahydrofuran-2-yl)methanol (Fluka, 4.0 g, 39.2 mmol) and di-tert-butyl hydrazine-1,2-dicarboxylate (9.1 g, 39.2 mmol) in THF (50 mL) was added triphenylphosphine (14.4 g, 54.8 mmol) followed by (E)-di-tert-butyl diazene-1,2-dicarboxylate (12.6 g, 54.8 mmol), portionwise. This mixture was stirred at ambient temperature for 16 h then was concentrated under reduced pressure and purified by column chromatography (SiO$_2$, 99% hex/EtOAc to 25% hex/EtOAc) to give the title compound (11.8 g, 37.3 mmol, 95% yield). MS (DCI/NH$_3$) m/z 317 (M+H)$^+$.

Example 10B (R)-((tetrahydrofuran-2-yl)methyl)hydrazine dihydrochloride

A mixture of the product of Example 10A (11.8 g, 37.3 mmol) and HCl (4 M in dioxane, 46.6 mL, 186 mmol) was stirred at ambient temperature for 16 h. The solids were isolated via filtration and were washed with Et$_2$O. The resulting title compound (6.4 g, 33.8 mmol, 91% yield) was carried on without further purification. MS (DCI/NH$_3$) m/z 117 (M+H)$^+$.

Example 10C (R)-3-tert-butyl-1-((tetrahydrofuran-2-yl)methyl)-1H-pyrazol-5-amine A mixture of the product of Example 10B (6.5 g, 34.4 mmol) and 4,4-dimethyl-3-oxopentanenitrile (4.3 g, 34.4 mmol) in ethanol (40 mL) was warmed to 85° C. and was allowed to stir for 4 h. The mixture was cooled to ambient temperature, concentrated under reduced pressure and the residue was dissolved in CH$_2$Cl$_2$ (10 mL) and saturated, aqueous NaHCO$_3$ (10 mL). The layers were separated and the aqueous layer was extracted with CH$_2$Cl$_2$ (3×10 mL). The combined organics were dried over anhydrous Na$_2$SO$_4$, filtered and concentrated under reduced pressure to provide crude title compound (7.8 g, 35.0 mmol, 102% yield) which was carried on without purification. MS (DCI/NH$_3$) m/z 224 (M+H)$^+$.

Example 10D

N-{3-tert-butyl-1-[(2R)-tetrahydrofuran-2-ylmethyl]-1H-pyrazol-5-yl}-2-fluoro-5-(trifluoromethyl)benzamide To a solution of the product of Example 10C (7.8 g, 35.0 mmol) and triethylamine (14.6 mL, 105 mmol) in THF (60 mL) at ambient temperature was added 2-fluoro-5-(trifluoromethyl)benzoyl chloride (5.3 mL, 35.0 mmol) dropwise over 10 min. The mixture was stirred at ambient temperature for 3 h. The mixture was quenched with saturated, aqueous NaHCO$_3$ (20 mL) and diluted with EtOAc (20 mL). The layers were separated and the aqueous layer was extracted with EtOAc (3×10 mL). The combined organics were dried over anhydrous Na$_2$SO$_4$, filtered and concentrated under reduced pressure. Purification by column chromatography (SiO$_2$, 40% hexanes/EtOAc) gave the title compound (11.0 g, 26.6 mmol, 76% yield). MS (DCI/NH$_3$) m/z 414 (M+H)$^+$.

Example 10E

N-{(3E)-5-tert-butyl-1-methyl-2-[(2R)-tetrahydrofuran-2-ylmethyl]-1,2-dihydro-3H-pyrazol-3-ylidene}-2-fluoro-5-(trifluoromethyl)benzamide A mixture of the product of Example 10D (14.2 g, 34.3 mmol) and dimethyl sulfate (9.9 mL, 103 mmol) in toluene (40 mL) was warmed to 90° C. and was allowed to stir for 18 h then was cooled to ambient temperature. The mixture was concentrated under reduced pressure and was purified by column chromatography (SiO$_2$, 50% hexanes/EtOAc to 100% EtOAc to 9:1:0.1 EtOAc:MeOH:Et₃N) to give the title compound (10 g, 23.4 mmol, 68% yield). MS (DCI/NH₃) m/z 428 (M+H)⁺.

Example 10F

N-{(3E)-5-tert-butyl-1-methyl-2-[(2R)-tetrahydrofuran-2-ylmethyl]-1,2-dihydro-3H-pyrazol-3-ylidene}-2-(2-fluoroethoxy)-5-(trifluoromethyl)benzamide Potassium t-butoxide (2.3 mL, 1M in THF) was added to 2-fluoroethanol (0.17 g, 2.5 mmol) in 1 mL of THF and stirred for 10 minutes. Example 10E in 2 mL of THF was added and the mixture stirred at amibient temperature for 1 hour. The mixture was diluted with dichloromethane (15 mL), 50 µL of glacial acetic acid was added, the solids were removed by filtration and the filtrate chromatographed, gradient eluting with solvents A:B (100:0 to 50:50) wherein solvent A=hexane:EtOAc:Et₃N (10:30:1); and solvent B=hexane:EtOAc:MeOH:Et₃N (10:30:10:1) to afford the title compound (0.4 g, 0.85 mmol, 73% yield). ¹H NMR (300 MHz, DMSO-d₆) δ ppm 1.38 (s, 9H), 1.66-1.79 (m, 3H), 1.79-1.91 (m, 1H), 3.58-3.66 (m, 1H), 3.69-3.79 (m, 1H), 3.88 (s, 3H), 4.11-4.21 (m, 1H), 4.25-4.30 (m, 1H), 4.30-4.39 (m, 3H), 4.60-4.66 (m, 1H), 4.76-4.82 (m, 1H), 6.81 (s, 1H), 7.18 (d, J=8.7 Hz, 1H), 7.59 (dd, J=8.7, 2.8 Hz, 1H), 7.73 (d, J=2.4 Hz, 1H). MS (DCI/NH₃) m/z 472.3 (M+H)⁺.

Example 10G

N-{(3E)-5-tert-butyl-1-methyl-2-[(2R)-tetrahydrofuran-2-ylmethyl]-1,2-dihydro-3H-pyrazol-3-ylidene}-2-(2-fluoroethoxy)-5-(trifluoromethyl)benzenecarbothioamide Lawesson's Reagent was added to Example 10F, (0.4 g, 0.85 mmol) in 8.5 mL of toluene and heated at 80° C. for 1 hour in a sealed tube. The solvent was removed and the residue redried twice from dichloromethane then chromatographed gradient eluting with solvents A:B (100:0 to 50:50) wherein solvent A=hexane:EtOAc:Et₃N (30:30:1); and solvent B=hexane:EtOAc:MeOH:Et₃N, (30:30:10:1) to afford the title compound. (0.32 g, 0.66 mmol, 77% yield). ¹H NMR (300 MHz, DMSO-d₆) δ ppm 1.41 (s, 9H), 1.62-1.77 (m, 3H), 1.77-1.88 (m, 1H), 3.56-3.64 (m, 1H), 3.72 (td, J=7.3, 6.1 Hz, 1H), 4.02 (s, 3H), 4.09-4.19 (m, 1H), 4.24-4.28 (m, 1H), 4.30-4.45 (m, 3H), 4.57-4.62 (m, 1H), 4.73-4.78 (m, 1H), 7.15 (d, J=9.5 Hz, 1H), 7.48-7.54 (m, 3H). MS (DCI/NH₃) m/z 488.2 (M+H)⁺.

Example 10H

N-{(3E)-5-tert-butyl-1-methyl-2-[(2R)-tetrahydrofuran-2-ylmethyl]-1,2-dihydro-3H-pyrazol-3-ylidene}-N'-cyano-2-(2-fluoroethoxy)-5-(trifluoromethyl)benzenecarboximidamide Example 10G, (0.32 g, 0.66 mmol), cyanamide (0.06 g, 1.3 mmol), mercuric acetate (0.27 g, 0.85 mmol), and triethylamine (0.25 mL, 1.8 mmol) were brought to reflux at 100° C. in 15 mL of acetonitrile for 90 minutes. The reaction was cooled, filtered through celite and silica, washed with acetonitrile and the solvent removed under reduced pressure. The residue was chromatographed gradient eluting with solvents A:B (100:0 to 50:50) wherein solvent A=hexane:EtOAc:Et₃N (30:30:1); and solvent B=hexane:EtOAc:MeOH:Et₃N, (30:30:10:1) to afford the title compound. (0.19 g, 0.38 mmol, 58% yield). ¹H NMR (300 MHz, DMSO-d₆) δ ppm 1.38 (s, 9H), 1.58-1.69 (m, 1H), 1.69-1.80 (m, 2H), 1.81-1.92 (m, 1H), 3.59-3.66 (m, 1H), 3.69-3.77 (m, 1H), 3.98 (s, 3H), 4.11-4.19 (m, 1H), 4.30-4.35 (m, 1H), 4.35-4.40 (m, 2H), 4.40-4.44 (m, 1H), 4.62-4.67 (m, 1H), 4.78-4.82 (m, 1H), 6.64 (s, 1H), 7.31 (d, J=8.8 Hz, 1H), 7.50 (d, J=2.0 Hz, 1H), 7.73 (dd, J=8.6, 1.9 Hz, 1H). MS (DCI/NH₃) m/z 496.3 (M+H)⁺. Analytical calculated for $C_{24}H_{29}F_4N_5O_2$: C, 58.17; H, 5.90; N, 14.13. Found: C, 58.15; H, 5.94; N, 14.18.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

The invention claimed is:
1. A compound having formula (I)

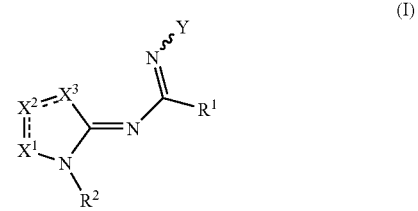

or a pharmaceutically acceptable salt thereof, wherein
$R^1$ is aryl, wherein the aryl is independently unsubstituted or substituted by 1, 2, 3, 4, or 5 substituents as represented by T, wherein each T is independently selected from the group consisting of alkyl, alkenyl, alkynyl, halogen, haloalkyl, —CN, —NO₂, oxo, -G¹, -L¹-A¹, —SR^a, —S(O)₂R^d, —S(O)₂N(R^b)(R^c), —C(O)R^a, —C(=NOR^{m1})R^a, —C(O)OR^a, —C(O)N(R^b)(R^c), —(CR^eR^f)_r—OR^a, —(CR^eR^f)_r—OC(O)R^a, —(CR^eR^f)_r—OC(O)N(R^b)(R^c), —(CR^eR^f)_r—SR^a, —(CR^eR^f)_r—S(O)₂R^d, —(CR^eR^f)_r—S(O)₂N(R^b)(R^c), —(CR^eR^f)_r—C(O)R^a, —(CR^eR^f)_r—C(=NOR^{m1})R^a, —(CR^eR^f)_r—C(O)OR^a, —(CR^eR^f)_r—C(O)N(R^b)(R^c), —(CR^eR^f)_r—N(R^b)(R^c), —(CR^eR^f)_r—N(R^c)C(O)R^a, —(CR^eR^f)_r—N(R^c)S(O)₂R^d, —(CR^eR^f)_r—N(R^c)C(O)O(R^d), —(CR^eR^f)_r—N(R^c)C(O)N(R^b)(R^c), —(CR^eR^f)_r-G¹, and —(CR^eR^f)_r—CN;
$A^1$ is $R^a$, —(CR^eR^f)_r-A², —C(O)R^a, —C(O)N(R^b)(R^c), S(O)₂R^d, C(O)O(R^d), —N(R^b)C(O)R^a, —N(R^b)C(O)OR^d, —N(R^b)(R^c), or —N=C(R^b)(R^c);
$A^2$ is —C(O)R^a, —S(O)₂R^d, —C(O)N(R^b)(R^c), —C(S)N(R^b)(R^c), —S(O)₂N(R^b)(R^c), —C(=NOR^{m1})R^a, —N(R^c)C(O)R^a, —N(R^c)C(O)OR^d, —N(R^c)S(O)₂R^d, —N(R^c)C(O)N(R^b)(R^c), —N(R^c)S(O)₂N(R^b)(R^c), or -L²-R^z;
$L^1$ and $L^2$ are each independently O or N(R^b);
$R^2$ is alkyl, alkenyl, alkynyl, haloalkyl, —(CR^gR^h)_t—OR^k, —(CR^gR^h)_t—O-G², —(CR^gR^h)_t—O—(CR^gR^h)_u-G², —(CR^gR^h)_u—C(O)—R^a, —(CR^gR^h)_u—C(=NOR^{m1})R^a, —(CR^gR^h)_t—SO₂—R^d, —(CR^gR^h)_t—N(R^b)SO₂R^d, —(CR^gR^h)_u-G³, —(CR^gR^h)_t—N(R^b)COR^a, —(CR^gR^h)_t—N(R^b)CON(R^b)(R^c), —(CR^gR^h)_t—N(R^b)SO₂N(R^b)(R^c), —(CR$^g$R$^h$)$_u$—SO$_2$N(R$^b$)(R$^c$), —(CR$^g$R$^h$)$_u$—C(O)N(R$^b$)(R$^c$), —(CR$^g$R$^h$)$_u$—OC(O)N(R$^b$)(R$^c$), or —(CR$^g$R$^h$)$_u$—CN;

X$^1$ is N, and X$^3$ is S wherein the bond between X$^1$ and X$^2$ is a double bond and the bond between X$^2$ and X$^3$ is a single bond;

X$^2$ is CR$^4$;

R$^3$ is hydrogen, alkyl, cycloalkyl, alkoxyalkyl, cyanoalkyl, or haloalkyl;

R$^{3a}$ is alkyl, cycloalkyl, alkoxyalkyl, cyanoalkyl, or haloalkyl;

R$^4$ is hydrogen, alkyl, alkylcarbonyl, alkenyl, alkynyl, cycloalkyl, cycloalkylalkyl, alkoxyalkyl, hydroxyalkyl, haloalkyl, halo, cyano, cyanoalkyl, or monocyclic heterocycle;

R$^5$ is hydrogen, alkyl, haloalkyl, halo, cyano, or alkoxyalkyl;

Y is CN or OR$^y$

R$^y$ is alkyl, G$^5$, or —(CR$^p$R$^q$)$_v$-G$^6$;

G$^1$, G$^2$ and G$^3$, at each occurrence, are each independently aryl, heteroaryl, cycloalkyl, cycloalkenyl, or heterocycle; wherein G$^1$, G$^2$, and G$^3$ are each independently unsubstituted or substituted with 1, 2, 3, 4, or 5 substituents independently selected from the group consisting of G$^4$, alkyl, alkenyl, alkynyl, halo, haloalkyl, =N—CN, =N—OR$^{m1}$, —CN, oxo, —NO$_2$, —OR$^m$, —OC(O)R$^m$, —OC(O)N(R$^m$)$_2$, —S(O)$_2$R$^n$, —S(O)$_2$N(R$^m$)$_2$, —C(O)R$^m$, —C(O)OR$^m$, —C(O)N(R$^m$)$_2$, —N(R$^m$)$_2$, —N(R$^m$)C(O)R$^m$, —N(R$^m$)S(O)$_2$R$^n$, —N(R$^m$)C(O)O(R$^n$), —N(R$^m$)C(O)N(R$^m$)$_2$, —(CR$^i$R$^j$)$_w$—OR$^m$, —(CR$^i$R$^j$)$_w$—OC(O)R$^m$, —(CR$^i$R$^j$)$_w$—OC(O)N(R$^m$)$_2$, —(CR$^i$R$^j$)$_w$—S(O)$_2$R$^n$, —(CR$^i$R$^j$)$_w$—S(O)$_2$N(R$^m$)$_2$, —(CR$^i$R$^j$)$_w$—C(O)R$^m$, —(CR$^i$R$^j$)$_w$—C(O)OR$^m$, —(CR$^i$R$^j$)$_w$—C(O)N(R$^m$)$_2$, —(CR$^i$R$^j$)$_w$—N(R$^m$)$_2$, —(CR$^i$R$^j$)$_w$—N(R$^m$)C(O)R$^m$, —(CR$^i$R$^j$)$_w$—N(R$^m$)S(O)$_2$R$^n$, —(CR$^i$R$^j$)$_w$—N(R$^m$)C(O)O(R$^m$), —(CR$^i$R$^j$)$_w$—N(R$^m$)C(O)N(R$^m$)$_2$, and —(CR$^i$R$^j$)$_w$—CN;

R$^p$ and R$^q$, at each occurrence, are each independently hydrogen or alkyl;

r and u, at each occurrence, are each independently 1, 2, 3, 4, 5, or 6;

t, at each occurrence, is independently 2, 3, 4, 5, or 6;

v is 1 or 2;

each occurrence of w is independently 1, 2 or, 3;

G$^4$ is monocyclic heterocycle, monocyclic heteroaryl, or monocyclic cycloalkyl;

G$^5$ and G$^6$, are each a monocyclic ring independently selected from the group consisting of cycloalkyl, heterocycle, heteroaryl, and phenyl;

R$^a$ and R$^c$, at each occurrence, are each independently hydrogen, alkyl, haloalkyl, alkoxyalkyl, hydroxyalkyl, cyanoalkyl, haloalkoxyalkyl, G$^1$, or —(CR$^e$R$^f$)$_r$-G$^1$;

R$^b$, at each occurrence, is independently hydrogen, alkyl, haloalkyl, alkoxyalkyl, cycloalkyl, or haloalkoxyalkyl;

R$^d$, at each occurrence, is independently alkyl, haloalkyl, alkoxyalkyl, hydroxyalkyl, cyanoalkyl, haloalkoxyalkyl, G$^1$, or —(CR$^e$R$^f$)$_r$-G$^1$;

R$^e$, R$^f$, R$^g$, R$^h$, R$^i$, and R$^j$, at each occurrence, are each independently hydrogen, alkyl, halogen, or haloalkyl;

R$^k$ is hydrogen, alkyl, haloalkyl, alkoxyalkyl, or haloalkoxyalkyl;

R$^z$ is alkoxyalkyl, hydroxyalkyl, cyanoalkyl, haloalkoxyalkyl, G$^1$, or —(CR$^e$R$^f$)$_r$-G$^1$;

R$^m$, at each occurrence, is independently hydrogen, alkyl, haloalkyl, —(CR$^e$R$^f$)$_q$—OR$^{m1}$, or monocyclic cycloalkyl;

R$^{m1}$, at each occurrence, is independently hydrogen, alkyl, haloalkyl, or monocyclic cycloalkyl;

R$^n$, at each occurrence, is independently alkyl, haloalkyl, cycloalkyl, or cycloalkylalkyl; and the cycloalkyl, heterocycle, heteroaryl, and phenyl, by itself of as part of a substituent, of R$^3$, R$^{3a}$, R$^4$, G$^4$, G$^5$, G$^6$, R$^b$, R$^m$, R$^{m1}$, and R$^{m1}$, are each independently unsubstituted or substituted with 1, 2, 3, or 4 substituents selected from the group consisting of alkyl, haloalkyl, alkoxy, halo, oxo, cyano, and hydroxy.

2. The compound according to claim 1 having formula (II), or a pharmaceutically acceptable salt thereof,

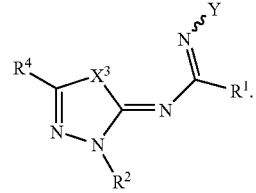

(II)

3. The compound according to claim 1 or a pharmaceutically acceptable salt thereof, wherein R$^3$ is hydrogen, alkyl, monocyclic cycloalkyl, or haloalkyl;

R$^{3a}$ is alkyl or haloalkyl;

R$^4$ is hydrogen, alkyl, alkenyl, alkynyl, monocyclic cycloalkyl, haloalkyl, or monocyclic heterocycle; and R$^5$ is hydrogen, alkyl, haloalkyl, or halo.

4. The compound according to claim 1 or a pharmaceutically acceptable salt thereof, wherein R$^1$ is phenyl substituted by 1, 2, 3, 4, or 5 substituents as represented by T.

5. The compound according to claim 1 or a pharmaceutically acceptable salt thereof, wherein Y is CN.

6. The compound according to claim 1 or a pharmaceutically acceptable salt thereof, wherein Y is OR$^y$; and R$^y$ is alkyl.

7. The compound according to claim 2 or a pharmaceutically acceptable salt thereof, wherein R$^2$ is alkyl, alkenyl, alkynyl, haloalkyl, —(CR$^g$R$^h$)$_t$—OR$^k$, —(CR$^g$R$^h$)$_t$—O-G$^2$, —(CR$^g$R$^h$)$_t$—O—(CR$^g$R$^h$)$_u$-G$^2$, —(CR$^g$R$^h$)$_u$—C(O)—R$^a$, —(CR$^g$R$^h$)$_u$—C(=NOR$^{m1}$)R$^a$, —(CR$^g$R$^h$)$_u$-G$^3$, —(CR$^g$R$^h$)$_t$—N(R$^b$)SO$_2$R$^d$, —(CR$^g$R$^h$)$_t$—N(R$^b$)COR$^a$, —(CR$^g$R$^h$)$_t$—N(R$^b$)CON(R$^b$)(R$^c$), —(CR$^g$R$^h$)$_t$—N(R$^b$)SO$_2$N(R$^b$)(R$^c$), —(CR$^g$R$^h$)$_u$—SO$_2$N(R$^b$)(R$^c$), —(CR$^g$R$^h$)$_u$—C(O)N(R$^b$)(R$^c$), —(CR$^g$R$^h$)$_u$—OC(O)N(R$^b$)(R$^c$), or —(CR$^g$R$^h$)$_u$—CN;

R$^g$ and R$^h$ are each independently hydrogen or C$_1$-C$_4$ alkyl;

G$^2$ and G$^3$, at each occurrence, are each independently monocyclic heteroaryl, monocyclic cycloalkyl, or monocyclic heterocycle;

R$^4$ is hydrogen, alkyl, alkenyl, alkynyl, monocyclic cycloalkyl, haloalkyl, or monocyclic heterocycle;

R$^1$ is phenyl substituted by 1, 2, or 3, substituents as represented by T; and Y is CN.

8. The compound according to claim 7 or a pharmaceutically acceptable salt thereof, wherein R$^2$ is alkyl, —(CR$^g$R$^h$)$_u$-G$^3$, or —(CR$^g$R$^h$)$_u$—CN; and R$^4$ is alkyl, monocyclic cycloalkyl, or haloalkyl.

9. The compound according to claim 2 or a pharmaceutically acceptable salt thereof, wherein
$R^2$ is alkyl, alkenyl, alkynyl, haloalkyl, —$(CR^gR^h)_t$—$OR^k$, —$(CR^gR^h)_t$—O-$G^2$, —$(CR^gR^h)_t$—O—$(CR^gR^h)_u$-$G^2$, —$(CR^gR^h)_u$—C(O)—$R^a$, —$(CR^gR^h)_u$—C(=NO$R^{m1}$)$R^a$, —$(CR^gR^h)_u$-$G^3$, —$(CR^gR^h)_t$—N($R^b$)SO$_2$$R^d$, —$(CR^gR^h)_t$—N($R^b$)CO$R^a$, —$(CR^gR^h)_t$—N($R^b$)CON($R^b$)($R^c$), —$(CR^gR^h)_t$—N($R^b$)SO$_2$N($R^b$)($R^c$), —$(CR^gR^h)_u$—SO$_2$N($R^b$)($R^c$), —$(CR^gR^h)_u$—C(O)N($R^b$)($R^c$), —$(CR^gR^h)_u$—OC(O)N($R^b$)($R^c$), or —$(CR^gR^h)_u$—CN;

$R^g$ and $R^h$ are each independently hydrogen or $C_1$-$C_4$ alkyl;

$G^2$ and $G^3$, at each occurrence, are each independently monocyclic heteroaryl, monocyclic cycloalkyl, or monocyclic heterocycle;

$R^4$ is hydrogen, alkyl, alkenyl, alkynyl, monocyclic cycloalkyl, haloalkyl, or monocyclic heterocycle;

$R^1$ is phenyl substituted by 1, 2, or 3 substituents as represented by T;

Y is O$R^y$; and $R^y$ is alkyl.

10. The compound according to claim 9 or a pharmaceutically acceptable salt thereof, wherein
$R^2$ is alkyl, —$(CR^gR^h)_u$-$G^3$, or —$(CR^gR^h)_u$—CN; and
$R^4$ is alkyl, monocyclic cycloalkyl, or haloalkyl.

11. The compound according to claim 1 or a pharmaceutically acceptable salt thereof, wherein
$R^2$ is alkyl, alkenyl, alkynyl, haloalkyl, —$(CR^gR^h)_t$—$OR^k$, —$(CR^gR^h)_t$—O-$G^2$, —$(CR^gR^h)_t$—O—$(CR^gR^h)_u$-$G^2$, —$(CR^gR^h)_u$—C(O)—$R^a$, —$(CR^gR^h)_u$—C(=NO$R^{m1}$)$R^a$, —$(CR^gR^h)_u$-$G^3$, —$(CR^gR^h)_t$—N($R^b$)SO$_2$$R^d$, —$(CR^gR^h)_t$—N($R^b$)CO$R^a$, —$(CR^gR^h)_t$—N($R^b$)CON($R^b$)($R^c$), —$(CR^gR^h)_t$—N($R^b$)SO$_2$N($R^b$)($R^c$), —$(CR^gR^h)_u$—SO$_2$N($R^b$)($R^c$), —$(CR^gR^h)_u$—C(O)N($R^b$)($R^c$), —$(CR^gR^h)_u$—OC(O)N($R^b$)($R^c$), or —$(CR^gR^h)_u$—CN;

$R^g$ and $R^h$ are each independently hydrogen or $C_1$-$C_4$ alkyl;

$G^2$ and $G^3$, at each occurrence, are each independently monocyclic heteroaryl, monocyclic cycloalkyl, or monocyclic heterocycle;

$R^3$ is hydrogen, alkyl, monocyclic cycloalkyl, or haloalkyl;

$R^4$ is hydrogen, alkyl, alkenyl, alkynyl, monocyclic cycloalkyl, haloalkyl, or monocyclic heterocycle;

$R^1$ is phenyl substituted by 1, 2, or 3, substituents as represented by T; and Y is CN.

12. The compound according to claim 11 or a pharmaceutically acceptable salt thereof, wherein
$R^2$ is alkyl, —$(CR^gR^h)_u$-$G^3$, or —$(CR^gR^h)_u$—CN;
$R^3$ is hydrogen, alkyl, or haloalkyl; and
$R^4$ is alkyl, monocyclic cycloalkyl, or haloalkyl.

13. The compound according to claim 1 or a pharmaceutically acceptable salt thereof, wherein
$R^2$ is alkyl, alkenyl, alkynyl, haloalkyl, —$(CR^gR^h)_t$—$OR^k$, —$(CR^gR^h)_t$—O-$G^2$, —$(CR^gR^h)_t$—O—$(CR^gR^h)_u$-$G^2$, —$(CR^gR^h)_u$—C(O)—$R^a$, —$(CR^gR^h)_u$—C(=NO$R^{m1}$)$R^a$, —$(CR^gR^h)_u$-$G^3$, —$(CR^gR^h)_t$—N($R^b$)SO$_2$$R^d$, —$(CR^gR^h)_t$—N($R^b$)CO$R^a$, —$(CR^gR^h)_t$—N($R^b$)CON($R^b$)($R^c$), —$(CR^gR^h)_t$—N($R^b$)SO$_2$N($R^b$)($R^c$), —$(CR^gR^h)_u$—SO$_2$N($R^b$)($R^c$), —$(CR^gR^h)_u$—C(O)N($R^b$)($R^c$), —$(CR^gR^h)_u$—OC(O)N($R^b$)($R^c$), or —$(CR^gR^h)_u$—CN;

$R^g$ and $R^h$ are each independently hydrogen or $C_1$-$C_4$ alkyl;

$G^2$ and $G^3$, at each occurrence, are each independently monocyclic heteroaryl, monocyclic cycloalkyl, or monocyclic heterocycle;

$R^{3a}$ is alkyl or haloalkyl;

$R^4$ is hydrogen, alkyl, alkenyl, alkynyl, monocyclic cycloalkyl, haloalkyl, or monocyclic heterocycle;

$R^5$ is hydrogen, alkyl, haloalkyl, or halo;

$R^1$ is phenyl substituted by 1, 2, or 3, substituents as represented by T; and Y is CN.

14. The compound according to claim 13 or a pharmaceutically acceptable salt thereof, wherein
$R^2$ is alkyl, —$(CR^gR^h)_u$-$G^3$, or —$(CR^gR^h)_u$—CN;
$R^{3a}$ is alkyl;
$R^4$ is alkyl, monocyclic cycloalkyl, or haloalkyl; and
$R^5$ is hydrogen.

15. The compound according to claim 1 or a pharmaceutically acceptable salt thereof, selected from the group consisting of
N-[(2Z)-3-butyl-5-tert-butyl-1,3,4-thiadiazol-2(3H)-ylidene]-5-chloro-N'-cyano-2-methoxybenzenecarboximidamide;
N-[(2Z)-5-tert-butyl-3-isobutyl-1,3,4-thiadiazol-2(3H)-ylidene]-5-chloro-N'-cyano-2-methoxybenzenecarboximidamide;
N-[(2Z)-5-tert-butyl-3-(1,3-thiazol-4-ylmethyl)-1,3,4-thiadiazol-2(3H)-ylidene]-5-chloro-N'-cyano-2-methoxybenzenecarboximidamide;
N-[(2Z)-5-tert-butyl-3-(3-cyanopropyl)-1,3,4-thiadiazol-2(3H)-ylidene]-5-chloro-N'-cyano-2-methoxybenzenecarboximidamide; and
N-[(2Z)-3-butyl-5-tert-butyl-1,3,4-thiadiazol-2(3H)-ylidene]-5-chloro-N,2-dimethoxybenzenecarboximidamide.

16. A pharmaceutical composition comprising a therapeutically effective amount of a compound of formula (I) according to claim 1 or a pharmaceutically acceptable salt thereof, in combination with a pharmaceutically acceptable carrier.

* * * * *